US011435486B2

(12) United States Patent
Penumadu et al.

(10) Patent No.: US 11,435,486 B2
(45) Date of Patent: Sep. 6, 2022

(54) FIBER AND BUNDLE ORIENTATIONS, MATRIX RICH REGIONS, AND MECHANICAL PROPERTIES OF FIBER REINFORCED COMPOSITES USING THERMAL DIGITAL IMAGE CORRELATION

(71) Applicant: University of Tennessee Research Foundation, Knoxville, TN (US)

(72) Inventors: Dayakar Penumadu, Knoxville, TN (US); Matthew Erich Kant, Knoxville, TN (US)

(73) Assignee: University of Tennessee Research Foundation, Knoxville, TN (US)

(*) Notice: Subject to any disclaimer, the term of this patent is extended or adjusted under 35 U.S.C. 154(b) by 110 days.

(21) Appl. No.: 16/562,108

(22) Filed: Sep. 5, 2019

(65) Prior Publication Data

US 2020/0072718 A1 Mar. 5, 2020

Related U.S. Application Data

(60) Provisional application No. 62/727,060, filed on Sep. 5, 2018.

(51) Int. Cl.
*B32B 41/00* (2006.01)
*G01T 1/167* (2006.01)
(Continued)

(52) U.S. Cl.
CPC .......... *G01T 1/167* (2013.01); *B29C 65/8253* (2013.01); *B29C 65/8261* (2013.01);
(Continued)

(58) Field of Classification Search
CPC ....... G01T 1/167; G01T 7/02; B29C 65/8253; B29C 65/8261; G01N 3/068; G01N 3/60; G01N 2033/0003
(Continued)

(56) References Cited

U.S. PATENT DOCUMENTS 5,102,690 A * 4/1992 Iyer .................. B05C 9/14
19/65 T
10,288,097 B2 5/2019 Ayuzawa et al.
(Continued)

OTHER PUBLICATIONS

Denos et al., "Progressive Failure Analysis in Platelet Based Composites Using CT-Measured Local Microstructure." SAMPE. 2017.
(Continued)

*Primary Examiner* — Michael N Orlando
*Assistant Examiner* — Joshel Rivera
(74) *Attorney, Agent, or Firm* — Jenkins, Wilson, Taylor & Hunt, P.A.

(57) ABSTRACT

Methods for assessing fiber and bundle orientations and mechanical properties of fiber reinforced composite materials using Thermal Digital Image Correlation (TDIC) are disclosed. In some examples, the method comprises exposing the composite material to a temperature change; imaging the composite material at a plurality of time points before, during and/or after the temperature change; and assessing the characteristic of the composite material based on the imaging. In others, temperature changes naturally occur during the cooling process after manufacturing can be employed for this method such as compression molding process, injection molding process, resin transfer molding processes and its variants.

22 Claims, 15 Drawing Sheets
(15 of 15 Drawing Sheet(s) Filed in Color)

(51) Int. Cl.
*G01T 7/02* (2006.01)
*B29C 65/82* (2006.01)
*G01N 3/06* (2006.01)
*G01N 3/60* (2006.01)
*G01N 33/00* (2006.01)

(52) U.S. Cl.
CPC ............... *G01N 3/068* (2013.01); *G01N 3/60* (2013.01); *G01T 7/02* (2013.01); *G01N 2033/0003* (2013.01)

(58) Field of Classification Search
USPC .................... 156/60, 64, 350, 351, 378, 379
See application file for complete search history.

(56) References Cited

U.S. PATENT DOCUMENTS

| | | | |
|---|---|---|---|
| 10,336,878 B2 | 7/2019 | Dellock et al. | |
| 10,370,509 B2 | 8/2019 | Mutsuda et al. | |
| 10,399,907 B2 | 9/2019 | Easter et al. | |
| 2018/0311914 A1* | 11/2018 | Marcoe | B29C 70/38 |
| 2019/0318444 A1* | 10/2019 | Juarez | B29C 70/384 |

OTHER PUBLICATIONS

Lee et al., "Characterization of fiber orientation in short fiber reinforced composites with an image processing technique," Materials Research Innovations, vol. 6(2), pp. 65-72 (2002).

Pradere et al., "Transverse and Longitudinal Coefficient of Thermal Expansion of Carbon Fibers at High Temperatures (300-2500 K)." vol. 46, pp. 1874-1884 (2008).

ASTM D3039 / D3039M—14 "Standard Test Method for Tensile Properties of Polymer Matrix Composite Materials," 13 pages, 2017.

Daniel et al., "Engineering Mechanics of Composite Materials." 2nd ed. 2005: Oxford University Press.

* cited by examiner

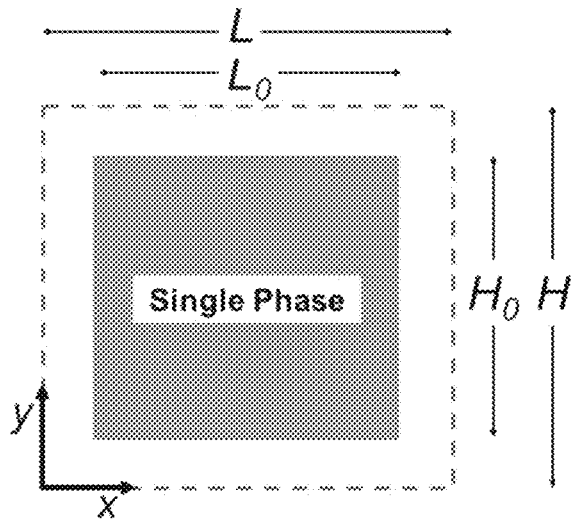
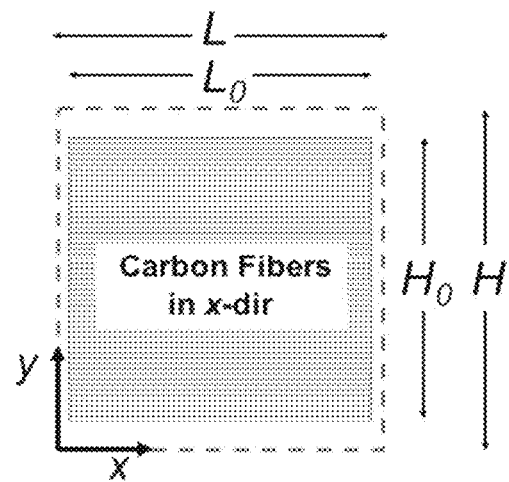
FIG. 3A        FIG. 3B
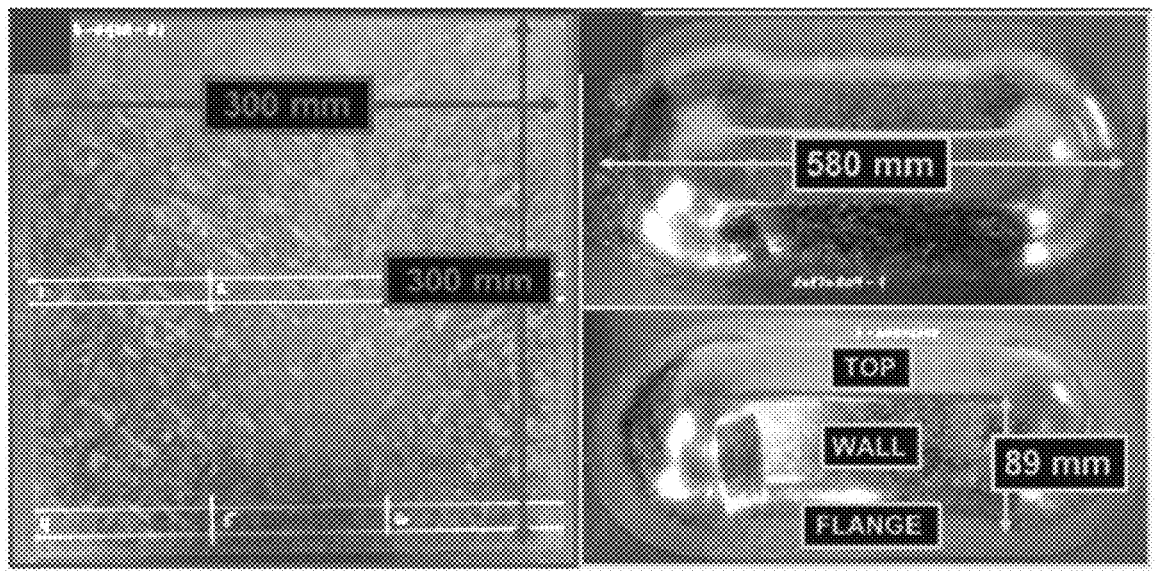
FIG. 4A        FIG. 4B

Procedure for DIC

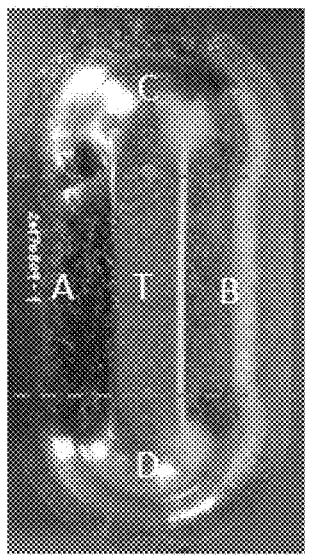

1. Double dome was discretized into 5 regions; A, B, C, D, and T.
2. Two cuts made along the dashed lines to split the part into 3 pieces.
3. Parts were painted and speckled with high contrast B/W pattern for DIC.
4. Initial (RT) images were taken.
5. Parts were put in oven at 100° C for an hour after which they were quickly removed and reimaged.
6. The resulting thermal expansions measured at the surface by DIC are proposed to be used to understand large part orientations.

FIG. 9

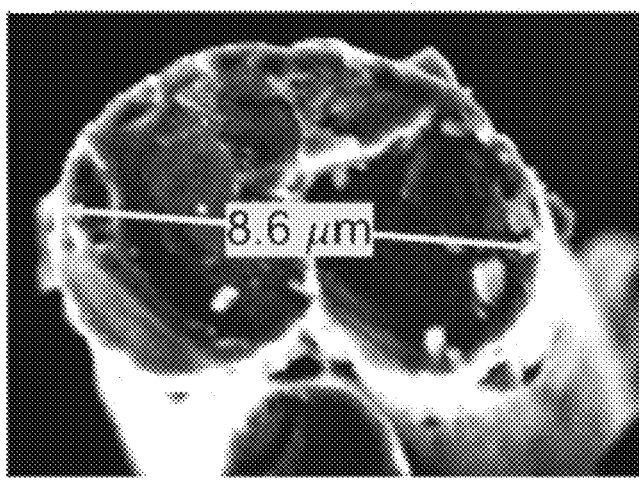 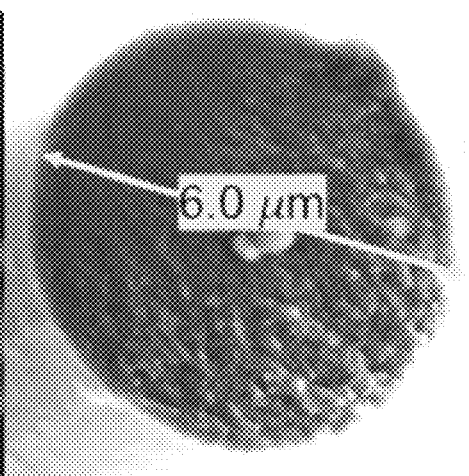

FIG. 10A  FIG. 10B 20170809-01 Side B Vector Map 20170809-03 Side B Vector Map

FIBER AND BUNDLE ORIENTATIONS, MATRIX RICH REGIONS, AND MECHANICAL PROPERTIES OF FIBER REINFORCED COMPOSITES USING THERMAL DIGITAL IMAGE CORRELATION

RELATED APPLICATIONS

The presently disclosed subject matter claims the benefit of U.S. Provisional Patent Application Ser. No. 62/727,060, filed Sep. 5, 2018; the disclosure of which is incorporated herein by reference in its entirety.

GOVERNMENT INTEREST

This invention was made with government support under Grant No. DE-EE0006926 awarded by the U.S. Department of Energy. The government has certain rights in the invention.

TECHNICAL FIELD

The presently disclosed subject matter relates to methods for analyzing composite materials. In particular, the presently disclosed subject matter relates to methods for analyzing fiber orientations, matrix regions, and bundle orientations and mechanical properties of fiber-reinforced composites using thermal digital imaging correlation (TDIC).

BACKGROUND

All materials at sufficiently small scales are inherently anisotropic, resulting from the distribution and orientation of microscopic representative compositional units, i.e. grains, fibers, or unit cells. If the compositional units are small and random, the material will behave isotopically on larger length scales. However, the mechanical performance of material strongly depends on the orientation and distribution of anisotropic micro- or meso-structural elements such as fibers. In many manufacturing techniques the final orientation is an outcome of the process and thus, necessitates quantification after formation to validate the material performance to design specifications. Current orientation measurement techniques are laborious, destructively invasive, costly and are limited to small spatial domains. This creates a significant limitation in the ability to validate performance at the part scale where predictive capability is challenging and a barrier to market entry, limiting the use of light weight, energy efficient materials for structural applications. Hence, there is a current need for rapid, non-destructive orientation evaluation for large spatial domains, including whole parts, for expeditious prototyping, engineering, and quality assessment to bring novel composite components to market, among other uses.

SUMMARY

In accordance with the presently disclosed subject matter, a method for assessing a characteristic of a composite material or a joint between two materials is disclosed. In some embodiments, the method comprises exposing the composite material or the joint to a temperature change; imaging the composite material or the joint at a plurality of time points before, during and/or after the temperature change; and assessing the characteristic of the composite material or the joint based on the imaging.

In some embodiments, the composite material comprises a fiber-reinforced composite material. In some embodiments, the composite material comprises a fiber-reinforced polymeric, metallic, or ceramic composite. In some embodiments, the composite material comprises a laminate/fabric based multi-layer composite material or a molded discontinuous fibers/bundles/platelets based composite material. In some embodiments, the composite material comprises a material selected from the group consisting of a thermoset-based carbon fiber, a thermoplastic-based carbon fiber, a glass fiber, a basalt fiber, a natural fiber, and combinations thereof. In some embodiments, the thermoset-based carbon fiber comprises a material selected from the group consisting of an epoxy, a vinyl ester, a polyester, a phenolic resin-based polymer, and combinations thereof. In some embodiments, the thermoplastic-based carbon fiber comprises a material selected from the group consisting of polyphenylene sulfide (PPS), polyether ether ketone (PEEK), acrylonitrile butadiene styrene (ABS), polyethylene terephthalate (PET), polypropylene, polycarbonate, polybutylene terephthalate (PBT, polyethylene, polyvinyl chloride (PVC), nylon, and combinations thereof.

In some embodiments, the joint is selected from the group consisting of a hybrid joint and an adhesively bonded joint.

In some embodiments, exposing the composite material to a temperature change comprises heating and/or cooling the composite material. In some embodiments, cooling the composite material comprises allowing the composite material to cool after manufacturing.

In some embodiments, the imaging comprises monitoring a surface mechanical strain tensor while the composite material is undergoing a temperature change. In some embodiments, the imaging comprises identifying spatially varying temperatures, identifying measured surface strains, or a combination thereof. In some embodiments, the imaging comprises applying indicia to the composite material and obtaining images of the composite material comprising the indicia. In some embodiments, the indicia comprise a contrasting black and white (B/W) pattern. In some embodiments, the imaging comprises using a thermal camera for measuring spatial temperatures and using an optical camera to obtain strain.

In some embodiments, the assessing the characteristic of the composite material based on the imaging comprises assessing fiber orientation of continuous fibers through a volume of the composite material. In some embodiments, the assessing the characteristic of the composite material based on the imaging comprises identifying spatially varied fiber orientations, matrix rich regions, corresponding mechanical properties, or combinations thereof. In some embodiments, the assessing the characteristic of the composite material comprises assessing manufacturing process control, quality assurance and/or control; predicting thermal behavior and/or mechanical behavior; and/or evaluating a repair.

In some embodiments, the method further comprises determining fiber orientation for a cross-section of the composite material grey-scale intensity changes. In some embodiments, the approach comprises using a variation of grey-scale intensity in relation to the orientation of considered plane of an image of the composite material. In some embodiments, the cross-section is a non-circular cross-section.

Provided in accordance with some embodiments of the presently disclosed subject matter is a method for assessing fiber orientation in a composite material or a joint between two materials. In some embodiments, the method comprises exposing the composite material or the joint to a light source; obtaining multiple images of the composite material or the joint; detecting differences in grey-scale intensity values from the multiple images; and assessing the fiber orientation of the composite material or the joint based on the differences in grey-scale intensity values. In some embodiments, the method comprises determining fiber orientation for a cross-section of the composite material or the joint using a variation of grey-scale intensity in the cross section of the composite material or the joint. In some embodiments, the cross-section is a non-circular cross-section. In some embodiments, the cross-section of the composite material or the joint that is selected comprises a reinforcing element or material having a non-circular cross-section. Fiber orientation of any of the composite materials and joints described herein can be assessed using these methods.

In some embodiments, a method of manufacturing a composite material is provided. In some embodiments, the method comprises during manufacturing of the composite material, exposing the composite material to a temperature change; imaging the composite material or at a plurality of time points before, during and/or after the temperature change; and assessing a characteristic of the composite material based on the imaging. In some embodiments, the method comprises controlling the manufacturing of the composite material based on the assessing of the characteristic of the composite material.

Thus, it is an object of the presently disclosed subject matter to provide methods for analyzing fiber and bundle orientations, matrix rich regions, micro/meso textured regions, and mechanical properties of fiber-reinforced composites using thermal digital imaging correlation (TDIC). An object of the presently disclosed subject matter having been stated herein above, and which is achieved in whole or in part by the presently disclosed subject matter, other objects will become evident as the description proceeds when taken in connection with the accompanying Figures as best described herein below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Preferred embodiments of the drawings will now be described of which:

FIGS. 3A and 3B are graphical representations of a 2-D element (pre-preg sheet for example in composites commu-nity) subjected to thermal loading with initial length, $L_0$, final length, L, initial height, $H_0$, and final height, H.

FIGS. 4A and 4B are a set of images showing examples of carbon fiber SMC parts from which samples were extracted. The flat plaque (FIG. 4A) has nearly random fiber orientation, while the more complex double dome (FIG. 4B) geometry has many regions of high orientation due to its complex molding geometry and flow induced fiber orientation during compression molding example case presented here of an example B-stage cured thermoset charge or thermoplastic charge made from discontinuous fiber reinforced composites.

FIG. 9 is a digital image showing an example of a composite material part with an image configuration for imaging in accordance with the presently disclosed subject matter.

FIGS. 10A and 10B are digital images showing a comparison of typical (FIG. 10A) Low-cost kidney bean shaped carbon fiber and (FIG. 10B) a reference Toray T700 round carbon fiber.

DETAILED DESCRIPTION

Figure 1:
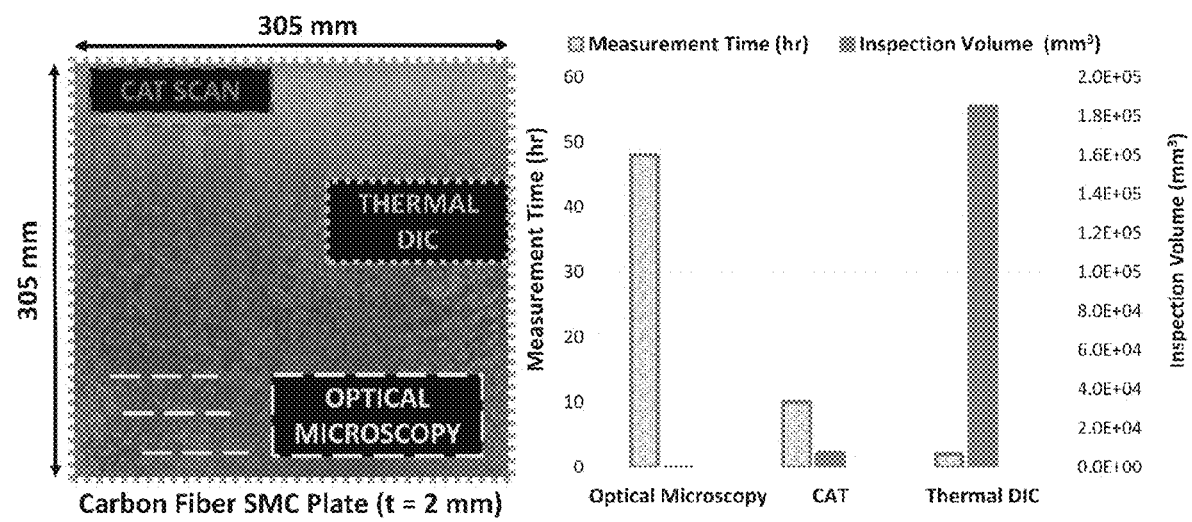
FIG. 1 is digital image (left panel) and graph (right panel) showing a comparison of temporal and spatial performance of current orientation and state of composite microstructure detection methods for CFRP systems. Potential samples are for all measurement techniques are shown on the left for an example flat panel part (dimensions provided in the Figure), while the relative effort to quantize these extracted samples is shown on the right. This demonstrates the significant advantages of TDIC technique of the presently disclosed subject matter for characterizing large and complex part geometries rapidly for performance prediction and quality control.

In accordance with the presently disclosed subject matter, a technique is presented herein which provides nondestructive information regarding the current condition of a manufactured part comprising anisotropic elements, such as but not limited to fiber presence, orientation, and/or relative amount of matrix volume fractions at target length scales. This information indicates orientation, potential failure modes, and deviation in design or targeted performance of composites. The presently disclosed subject matter can also be very useful as quality assurance and quality control methods for large volume and large scale production of composites. The methodology to extract potential zones of interest is described in detail, and as an initial demonstration, is then used to predict part failure for tensile coupons. In some embodiments, the presently disclosed subject matter examines example material systems, such as carbon fiber and epoxy matrix resin-based SMC (Sheet Molding Compound)'s. However, techniques in accordance with the presently disclosed subject matter are applicable to numerous material types broadly identified herein.

Techniques in accordance with the presently disclosed subject matter are also uniquely suited to identify matrix rich regions and fiber mis-orientation dominated regions in discontinuous and continuous fiber reinforced composites including sheet molding compound and bulk molding compound based components. Techniques in accordance with the presently disclosed subject matter can also be utilized for quality assurance and quality control of composites during manufacturing and usage in tow preg, UD tape, laminates, identifying spatially resolved state of composite information along adhesively or other ways of bonded joints (metal-composite, composite-composite, hybrid), and complex shaped molded components such as lift gates and deck lids in automotive applications.

Thermal and mechanical response of the fiber reinforced polymeric, metallic, and ceramic composites are strongly dependent on reinforcement fiber orientation and matrix resin rich zones within a composite. The fiber orientation of continuous fibers through the volume for laminate/fabric based multi-layer composites or molded discontinuous fibers/bundles/platelets based composites (for example, Sheet Molding Compounds or Bulk Molding Compounds) dictates the stiffness and strength along a given direction. The presently disclosed subject matter provides Thermal Digital Image Correlation (TDIC) methods with which one can image a fiber reinforced composite part or material, such as thermoset—(examples included epoxy or vinyl ester or polyester or phenolic resin based polymers) or thermoplastic—(examples include polyphenylene sulfide (PPS), polyether ether ketone (PEEK), acrylonitrile butadiene styrene (ABS), polyethylene terephthalate (PET), polypropylene, polycarbonate, polybutylene terephthalate (PBT, polyethylene, polyvinyl chloride (PVC), nylon, and combinations thereof) based carbon fiber, glass fiber, basalt fibers, and/or natural fiber composites, and can monitor the surface mechanical strain tensor while the part is cooling or heating. Exemplary data for continuous and chopped carbon fiber-based composites using epoxy as the matrix resin system are provided herein.

The presently disclosed Thermal Digital Image Correlation (TDIC) methods are robust and fast techniques that can be applied on small or large area based composite parts to quickly identify spatially variation fiber orientations, matrix rich regions, and corresponding mechanical properties. The presently disclosed Thermal Digital Image Correlation (TDIC) methods can be utilized for manufacturing process control, quality assurance and control, and predictive thermal and mechanical behavior for optimizing manufacturing process and thermal and mechanical properties including thermal conductivity, diffusivity and specific heat for thermal properties, stiffness and strength (static, dynamic, crashworthiness, fatigue, and fracture) for mechanical properties.

A method that accounts for spatially varying temperatures and measured surface strains is then used to estimate the representative fiber orientation spatially and identify interesting features such as potential matrix rich regions among others to predict mechanical performance. This method will also be applicable for evaluating repairs in composites (for example patch repairs and qualification) and hybrid joints (metal-composite, composite-composite). In joints (for example, adhesively bonded joints), the two similar or dissimilar materials being joined have to maintain very precise geometric tolerances and thermal expansion variation as a function of local variations in fiber orientation and/or matrix rich regions. Fiber orientation and/or matrix rich regions will impact such joints' performance post painting process, such as an E-coat process, with large thermal distortions. In some embodiments, the presently disclosed TDIC methods can be used to identify location specific mesostructured information, which can then utilized in design for proper joining. The presently disclosed TDIC methods can also be used for evaluating the thermal distortions spatially and precisely.

I. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the presently disclosed and claimed subject matter.

Definitions of particular chemical terms are those that would be understood by one of ordinary skill in the art. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in, for example, Sorrell, 2006; Smith & March, 2001; Larock, 1989; and Carruthers, 1986; the entire contents of each of which are incorporated herein by reference.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

Following long-standing patent law tradition, the terms "a", "an", and "the" are meant to refer to one or more as used herein, including the claims. For example, the phrase "a composite material" can refer to one or more composite materials. Also as used herein, the term "another" can refer to at least a second or more.

The use of the term "or" in the claims is used to mean "and/or" unless explicitly indicated to refer to alternatives only or the alternatives are mutually exclusive.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration, or percentage, is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the disclosed compositions. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. It is noted that, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising", "consisting of", and "consisting essentially of", where one of these three terms is used herein, the presently disclosed and claimed subject matter can include the use of either of the other two terms.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, "significance" or "significant" relates to a statistical analysis of the probability that there is a non-random association between two or more occurrences. To determine whether or not a relationship is "significant" or has "significance", statistical manipulations of the data can be performed to calculate a probability, expressed as a "p-value". Those p-values that fall below a user-defined cutoff point are regarded as significant. In some embodiments, a p-value less than or equal to 0.10, in some embodiments less than or equal to 0.05, in some embodiments less than or equal to 0.01, in some embodiments less than or equal to 0.005, and in some embodiments less than or equal to 0.001, are regarded as significant.

II. General Considerations

The current fiber orientation measurement state-of-the-art, specifically for CFRPs (Carbon Fiber Reinforced Plastics), relies on direct imaging techniques, i.e. the interaction of the material with various wavelengths of the electromagnetic spectrum to create an image based on the contrast between fibers and resin either by the reflection of visible light (400-700 nm) off a polished cross-sectional surface or the absorption of a broadband X-Ray (0.01-10 nm) beam for Computer Aided Tomography (CAT). In order to observe small diameter fibers (5-7 microns), exceptional spatial resolutions are required, which inherently, limits the field of view. In general, sample extraction and polishing for optical microscopy or CAT is laborious, inefficient, and gives a limited field of view. Thus, destructive imaging techniques for orientation mapping, are not adequate for understanding the performance of a whole part in high through-put, scaled-up production facilities, typical of penetrable markets where composites light-weighting applications are relevant. Hence, the feasibility of imaging techniques limited to strictly R&D and academic purposes due to time and efficiency are demonstrated in FIG. 1. It is noted that a complete three-dimensional mapping of part phases is sufficient condition to understand and predict performance, but not necessary or feasible one.

Conventional Non-Destructive Evaluation (NDE) probes a materials response to an input energy either mechanical (ultrasonic Time-Of-Flight (TOF)) or electrical (eddy current) to locate flaws spatially in a part. These techniques scan the surface of a material and are effective at detecting internal inhomogeneities, but do not give information regarding the performance of the part.

III. Methods

In some embodiments, the presently disclosed methods provide for characterizing in a rapid fashion the behavior of composite materials with anisotropic phases present inside. This characterization detects weaknesses in a final part and the loading to which this part would be most susceptible, too. In a predictive and semi-quantitative manner, the magnitude of failure can be determined. For instance, if a particular failure mode was of interest, the presently disclosed methods can indicate the most likely region for that failure and can provide information regarding its magnitude relative to an ideal part or standard.

In accordance with the presently disclosed subject matter, a method for assessing a characteristic of a composite material or a joint between two materials is disclosed. In some embodiments, the method comprises exposing the composite material or the joint to a temperature change; imaging the composite material or the joint at a plurality of time points before, during and/or after the temperature change; and assessing the characteristic of the composite material or the joint based on the imaging. In some embodiments, the joint is selected from the group consisting of a hybrid joint and an adhesively bonded joint.

In some embodiments, the composite material comprises a fiber-reinforced composite material. In some embodiments, the composite material comprises a fiber-reinforced polymeric, metallic, or ceramic composite. In some embodiments, the composite material comprises a laminate/fabric based multi-layer composite material or a molded discontinuous fibers/bundles/platelets based composite material. In some embodiments, the composite material comprises a material selected from the group consisting of a thermoset-based carbon fiber, a thermoplastic-based carbon fiber, a glass fiber, a basalt fiber, a natural fiber, and combinations thereof. In some embodiments, the thermoset-based carbon fiber comprises a material selected from the group consisting of an epoxy, a vinyl ester, a polyester, a phenolic resin-based polymer, and combinations thereof. In some embodiments, the thermoplastic-based carbon fiber comprises a material selected from the group consisting of polyphenylene sulfide (PPS), polyether ether ketone (PEEK), acrylonitrile butadiene styrene (ABS), polyethylene terephthalate (PET), polypropylene, polycarbonate, polybutylene terephthalate (PBT, polyethylene, polyvinyl chloride (PVC), nylon, and combinations thereof.

In some embodiments, the imaging comprises monitoring a surface mechanical strain tensor while the composite material is undergoing a temperature change. In some embodiments, the imaging comprises identifying spatially varying temperatures, identifying measured surface strains, or a combination thereof. In some embodiments, the imaging comprises applying indicia to the composite material and obtaining images of the composite material comprising the indicia. In some embodiments, the indicia comprise a contrasting black and white (B/W) pattern. In some embodiments, the imaging comprises using a thermal camera for measuring spatial temperatures and using an optical camera to obtain strain.

In some embodiments, the assessing the characteristic of the composite material based on the imaging comprises assessing fiber orientation of continuous fibers through a volume of the composite material. In some embodiments, the assessing the characteristic of the composite material based on the imaging comprises identifying spatially varied fiber orientations, matrix rich regions, corresponding mechanical properties, or combinations thereof. In some embodiments, the assessing the characteristic of the composite material comprises assessing manufacturing process control, quality assurance and/or control; predicting thermal behavior and/or mechanical behavior; and/or evaluating a repair.

In some embodiments, exposing the composite material to a temperature change comprises heating and/or cooling the composite material. In some embodiments, cooling the composite material comprises allowing the composite material to cool after manufacturing. Thus, in some embodiments, the presently disclosed methods involve monitoring the thermal deformations of a part exposed to isothermally heating (or cooling) to target temperature(s). In some embodiments, temperature changes naturally occur during the cooling process after manufacturing and can be employed, such as compression molding process, injection molding process, resin transfer molding processes and its variants. Additional examples of implementation of TDIC include the manufacturing/synthesis of reinforced thermoplastic and thermoset lamina, laminates, its variant form called organosheets, multi-step processing of metallic materials such as microtextured Ti based alloys, metal-matrix composite sheet stock. By way of an additional, non-limiting example when aerospace grade prepreg or automotive organosheets are made, typically one starts from continuous fiber in a sheet or mat form and reinforces with resin in a continuous or batch process. Challenges still exist with respect to properly reinforcing resin, such as high temperature thermoplastics and high glass transition thermosets into small void or inter fiber and inter bundle spacing, while attempting to eliminate air or defects. A TDIC approach in accordance with the presently disclosed subject matter can be used as a part of manufacturing process control.

In some embodiments, a method of manufacturing a composite material is provided. In some embodiments, the method comprises during manufacturing of the composite material, exposing the composite material to a temperature change; imaging the composite material or at a plurality of time points before, during and/or after the temperature change; and assessing a characteristic of the composite material based on the imaging. In some embodiments, the method comprises controlling the manufacturing of the composite material based on the assessing of the characteristic of the composite material. In some embodiments the temperature change can be natural during cross linking or polymerization process or externally applied from sources such as heat or IR lamps as non-limiting examples. Any of the composite materials described herein can be assessed and manufactured using these methods In the following example data step, ~75-100° C. represent a range of target temperatures. In some embodiments, the presently disclosed methods comprise heating (or cooling), including isothermal heating (or cooling) to target temperatures below typical glass transition temperatures of material in the composite material and/or joint to be assessed. However, any suitable temperature or temperature range can be selected, such as based on the composite material or joint to be assessed and as would be apparent to one of ordinary skill in the art upon a review of the instant disclosure. A simple linear relationship as shown in Equation (Eq.) 1 can be used to reliably describe the 1-D thermal expansion in this temperature range, where α represents the Coefficient of Thermal Expansion or CTE, ε is the strain, and ΔT is the temperature differential. Also, in some embodiments, strain is defined as in Eq. 2 for the 1-D element in FIG. 2, which is sufficient for the relatively small strains generated by thermal expansions at these temperatures.

TABLE 1

Expansion of uniaxial element exposed to thermal load, ΔT.

$\epsilon_x = \alpha_x(T - T_0) = \alpha_x \Delta T$  Eq. 1

$\epsilon_x = \dfrac{L - L_0}{L_0} = \dfrac{\Delta L}{L_0}$  Eq. 2

Similarly, for a 2-D isotropic material, thermal strains occur in all directions uniformly as FIG. 3A. Hence, an isotropic, homogenous material undergoing uniform, unconfined thermal loading will produce strains equivalent from all orientations. However, the introduction of anisotropic elements, for instant carbon fibers, alters the thermal expansion behavior relative to constituent's individual anisotropic thermal expansions as demonstrated in FIG. 3B. Here, negative axial thermal expansion of carbon fibers causes a smaller expansion in the x-direction (x-dir), the fiber direction, and the smaller radial expansion reduces the expansion in y-direction (y-dir) relative to the single phase.

Figure 2:
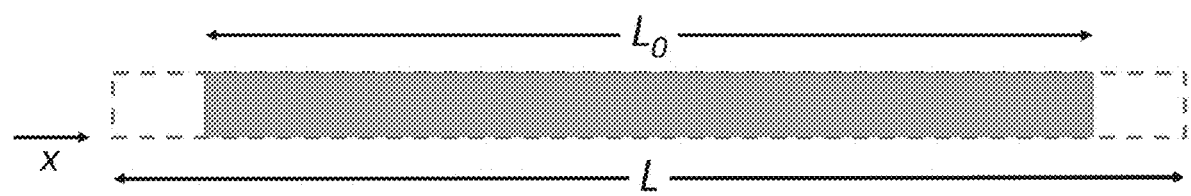
FIG. 2 is a graphical representation of a 1-D element subjected to thermal loading, in this example case of increase in temperature, with initial length, $L_0$, and final length, L.

FIGS. 2, 3A, and 3B schematically show plane stress and introduce 1D and 2D orientated properties and anisotropy. Materials that have distributed spatial anisotropy also have mechanical behaviors that reflect this distribution. Isotropic materials expand isotropically when exposed to elevated temperatures. If the distribution of anisotropy is random then at a particular scale the part actually behaves mechanically as if isotropic in structure. However, when regions have locally preferred orientations, the thermal deformations contain information regarding this internal structure and therefor some predictive material behavior.

Generally, when parts are designed, the material selected is expected to perform to the specification given by the manufacturer. However, in some embodiments, the presently disclosed subject matter does not attempt to map the precise fiber or tow (agglomerated fibers) orientations inside the whole region of interest, but rather resolves spatial locations where the material behavior appears to exhibit a preferred orientation. In some embodiments, the presently disclosed methodology considers the following concepts of importance to fiber reinforced materials: orientation dominated performance, mechanical strains from Digital Image Correlation using one or more optical cameras, thermal anisotropy, deviation from mechanical isotropy, orientation states from principle strains, mechanical failure prediction, predicted orientation states based upon known orientation inputs.

Figure 20:
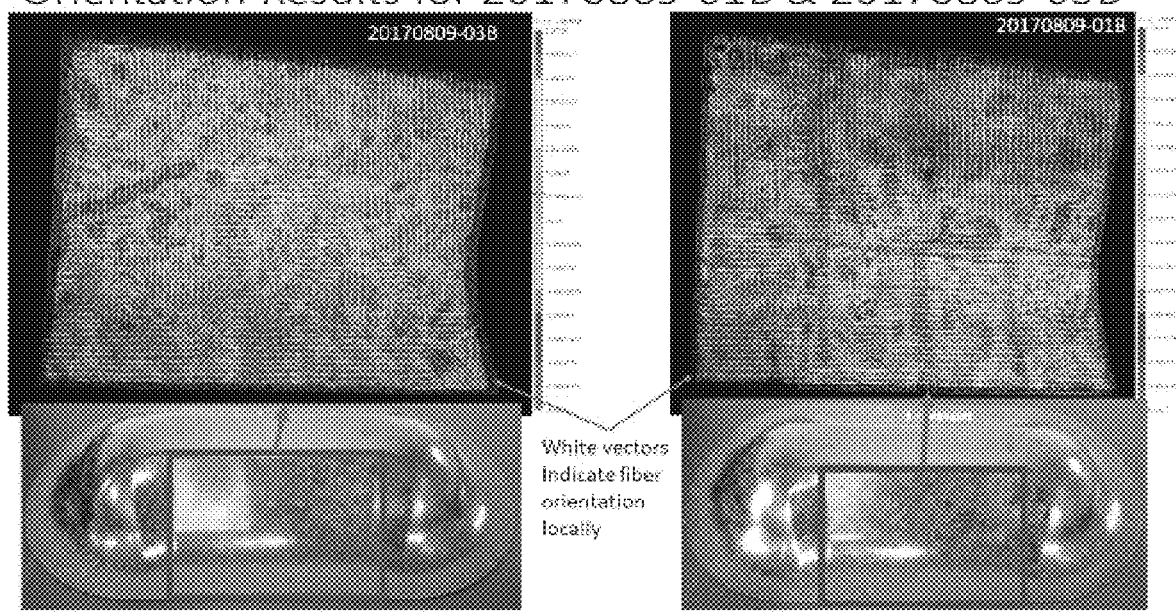
FIG. 20 is a set of graphical images and digital images showing examples of a composite material part with an image configuration for imaging in accordance with the presently disclosed subject matter.
Figure 21:
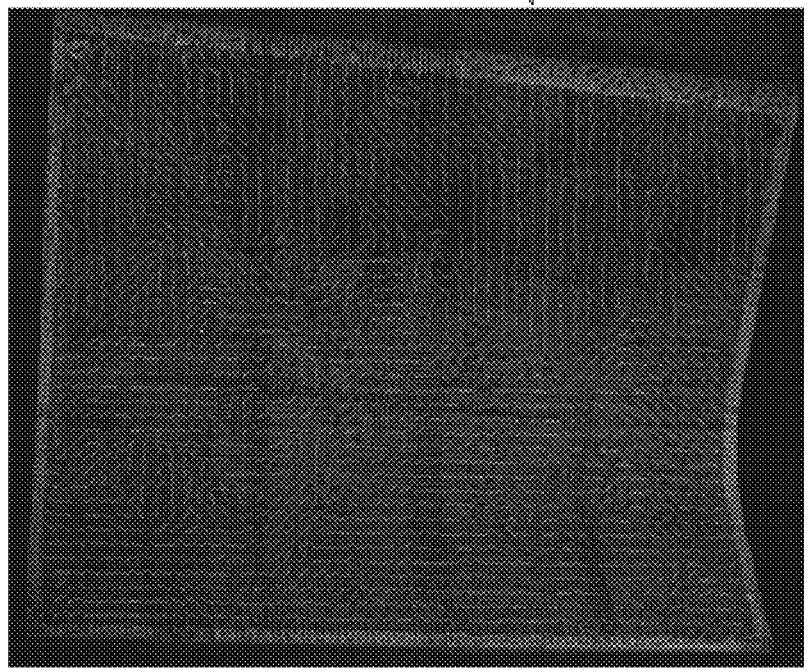
FIG. 21 is an image showing a surface vector map of fiber orientations obtained from the TDIC method in accordance with the presently disclosed subject matter.
Figure 22:
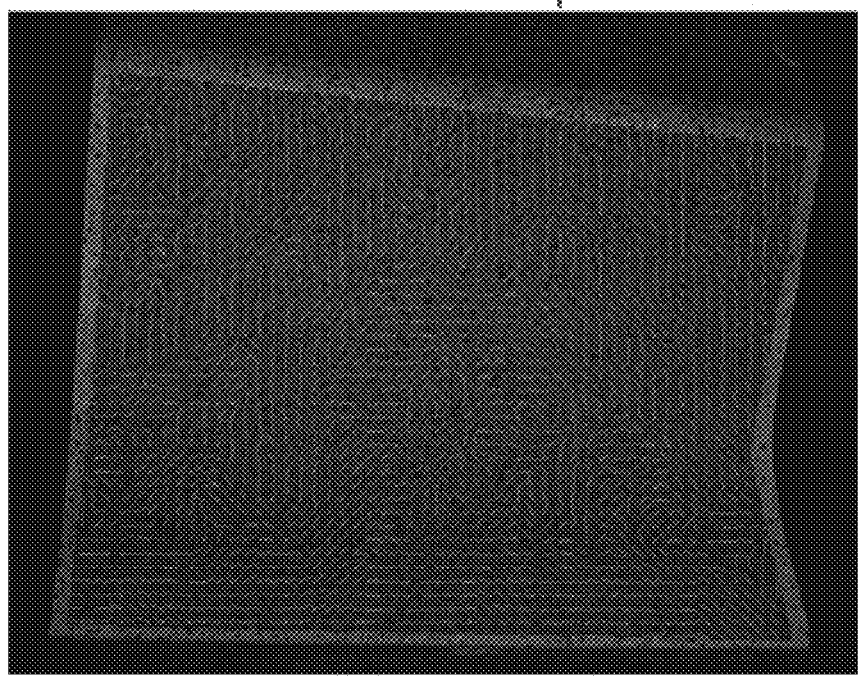
FIG. 22 is an image showing surface vector maps of fiber orientations obtained from the TDIC method in accordance with the presently disclosed subject matter.

Referring now to FIG. 9, a molded double dome shaped carbon fiber platelet-based compression molded composite part is presented. The part was discretized into five (5) regions: A, B, C, D, and T. Two cuts were made along the dashed lines to splits the part into three (3) pieces. The pieces of the parts were painted and speckled with a high contrast black and white (B/W) pattern for DIC. Initial (room temperature, RT) images were taken. The pieces of the part were put into an oven at 100° C. for an hour, after which they were quickly removed and reimaged. The resulting thermal expansions measured at the surface by DIC are used to understand large part orientations. Thus, FIG. 9 details the procedure, quantification of major and minor principal strains due to controlled change in temperature, and resultant fiber orientations for two example regions within the complex and large composite part. Regions A and B in FIG. 9 were evaluated to provide the example data included in FIGS. 20-22. FIG. 20 shows the magnitude and direction of the minor principal strain spatially for this molded component corresponding to two example sections identified. The direction of white arrows indicates the local orientation of carbon fiber reinforcement. The color values indicate its magnitude using the color scale shown in FIG. 20. For the two sides, FIGS. 21 & 22 shows local orientations of carbon fiber using vector contour plot which clearly shows regions of local preferred orientation of carbon fiber reinforcement. The strength and stiffness of composite normal to this direction will be weakest as it will be largely dominated by matrix resin, epoxy for the material considered in this study.

In addition to obtaining local fiber orientation of continuous and discontinuous fiber reinforced composites, equally important information associated with matrix rich regions and/or void rich regions can be identified with TDIC methods in accordance with the presently disclosed subject matter. Indeed, any change in the local material state can be spatially resolved with this technique. Additionally, by using a thermal camera for measuring spatial temperatures and one or more optical cameras, in some embodiments, two or more optical cameras, to obtain strain, one can use different lenses to capture small region or interest or large region of interest thus having the ability to view or characterize small or large composites with judicious choice of cameras and lenses.

Figure 23:
FIG. 23 is a photograph showing a test set up with large complex shape for a system suitable for carrying out a method in accordance with the presently disclosed subject matter.
Figure 24:
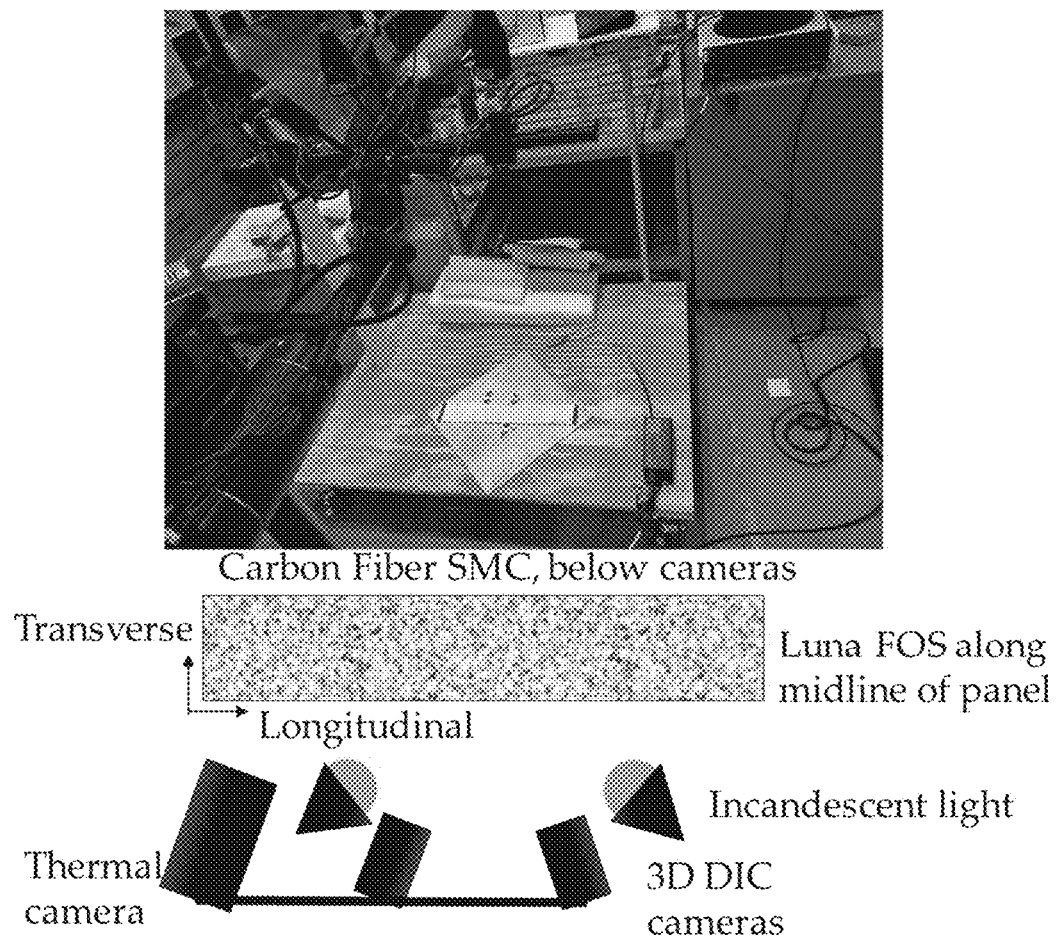
FIG. 24 is a photograph and a schematic showing a test set up with flat panel shape for a system suitable for carrying out a method in accordance with the presently disclosed subject matter.

Referring now to FIG. 23, a liftgate part LP from compression molding of composite is shown, subjected to TDIC measurements using a system S comprising a three-camera system TCS comprising a thermal camera and two optical cameras with special lighting that minimizes glare from reflections of ambient light. Referring to FIG. 24, another example of an experimental system S for thermal digital image correlation (TDIC) that shows schematically a form of camera system TCS comprising a thermal camera TC and two optical cameras DC (which can be 3D DIC cameras) and imaging a flat sheet FS of composite (carbon fiber SMC) that has been instrumented with a high definition fiber optic sensor HD-FOS along the midline of the panel FS for comparative data analysis and imaging in the transverse T and longitudinal L directions. Incandescent lights IL are also shown. The systems S shown in FIGS. 23 and 24 are operably connected to a control system (not shown), such as a computer, for controlling operation of the camera system TCS, lights IL, and image and data capture. Exposure of parts LP and FS to temperature changes occurs, in some embodiments, in an oven as described in the Examples set forth herein below, or in a manufacturing system for each part. Box MP schematically represents an oven or a manufacturing process and is configured for integration with a system like system S for carrying out a process in accordance with the presently disclosed subject matter using recognized techniques as disclosed herein, including manual steps by user and/or automated steps, and as would be apparent to one of ordinary skill in the art upon a review of the instant disclosure. Representative non-limiting manufacturing processes are also disclosed in U.S. Pat. Nos. 10,399,907, 10,336,878; 10,288,097 and 10,370,509, herein incorporated by reference in their entireties.

In some embodiments, the method further comprises determining fiber orientation for a cross-section of the composite material grey-scale intensity changes. In some embodiments, the approach comprises using a variation of grey-scale intensity in relation to the orientation of considered plane of an image of the composite material. In some embodiments, the cross-section is a non-circular cross-section.

Provided in accordance with some embodiments of the presently disclosed subject matter is a method for assessing fiber orientation in a composite material or a joint between two materials. In some embodiments, the method comprises exposing the composite material or the joint to a light source; obtaining multiple images of the composite material or the joint; detecting differences in grey-scale intensity values from the multiple images; and assessing the fiber orientation of the composite material or the joint based on the differences in grey-scale intensity values. In some embodiments, the method comprises determining fiber orientation for a cross-section of the composite material or the joint using a variation of grey-scale intensity in the cross section of the composite material or the joint. In some embodiments, the cross-section is a non-circular cross-section. In some embodiments, the cross-section of the composite material or the joint that is selected comprises a reinforcing element or material having a non-circular cross-section.

Fiber orientation of any of the composite materials and joints described herein can be assessed using these methods.

EXAMPLES

The following EXAMPLES provide illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Example 1

Method for Rapid Determination of Fiber Orientation in Reinforced Composites at Lab and Component Scale In accordance with the presently disclosed subject matter, this Example provides a Thermal Digital Image Correlation (TDIC) method with which one can image a fiber reinforced composite materials including epoxy, vinyl ester, polyester, phenolic, or thermoplastic resin with carbon fiber, glass fiber, basalt fiber or natural fiber reinforcements. This Example involves monitoring the surface mechanical strain tensor, while the part is cooling or heating.

This Example provides data for continuous and chopped carbon fiber-based composites using epoxy as the matrix resin system has been developed. TDIC is a robust and fast technique that can be applied on small or large area based composite parts to quickly identify spatially variation fiber orientations, matrix rich regions, and corresponding mechanical properties. This technique can be utilized for manufacturing process control, quality assurance and control, and predictive thermal and mechanical behavior for optimizing manufacturing processes and thermal and mechanical properties including thermal conductivity, diffusivity and specific heat for thermal properties, stiffness and strength (static, dynamic, crashworthiness, fatigue, and fracture).

The current state-of-the-art associated with fiber orientation measurement, specifically for CFRPs (Carbon Fiber Reinforced Plastics), relies on direct imaging techniques. In general, sample extraction and polishing for optical microscopy or lab scale X-ray tomography is laborious, inefficient, and gives a limited field of view (Benjamin et al., *Progressive Failure Analysis in Platelet Based Composites Using CT-Measured Local Microstructure*, in SAMPE. 2017; Lee, Y., et al., Materials Research Innovations, 2002. 6(2): p. 65-72). Thus, the current destructive imaging techniques for orientation mapping are not adequate for understanding the performance of a whole part in high through-put, scaled-up production facilities, typical of penetrable markets where fiber reinforced composites light-weighting applications are relevant. FIG. 1 demonstrates graphically a relative comparison between current techniques of the approximate effort in time required to acquire orientation state of a material and the amount of material volume inspected.

In accordance with the presently disclosed subject matter, the TDIC method explored in this Example relies on monitoring the spatially resolved thermal deformations of a part exposed to isothermal heating (or cooling) to target temperatures well below typical resin glass transition temperatures, ~75-100° C. for epoxy type system for example. FIGS. 3A and 3B of a UD composite demonstrate the differences in thermal expansions as a result of fiber orientation. A demonstration of applying this logic to larger more complex systems is presented with comparisons to conventional orientation techniques. Due to large anisotropy of thermal expansion coefficient for carbon fibers along and across the fiber length, this method is very suitable for carbon fiber-based composites.

Results/Discussion

The methods evaluated in this Example are used to detect fiber orientation rapidly on large parts. Table 2 lists the samples used here for demonstration and that were selected to give a variation of responses to observe the sensitivity of the technique. SMC fiber composites can have many orientation states from almost fully orientated to random, which depends on the manufacturing conditions and also, supports the need for a simple, rapid characterization approach. Generally, if more material flow occurs during the molding process, then more regions of high orientation will be expected.

TABLE 2

List of samples used for demonstration of TDIC technique.

| SAMPLE | Matrix | Process | Geometry |
| --- | --- | --- | --- |
| UD plate | Epoxy | Pultrusion | 2 × 2 In. |
| Platelet SMC (plaque mold) | Epoxy | Compression Molded | 4 × 0.5 In. |
| Platelet SMC (Double Dome mold) | Epoxy | Compression Molded | 4 × 0.5 In. |
| Fiber mat SMC | PPS | Compression Molded | 4 × 4 In. |

Figure 5:
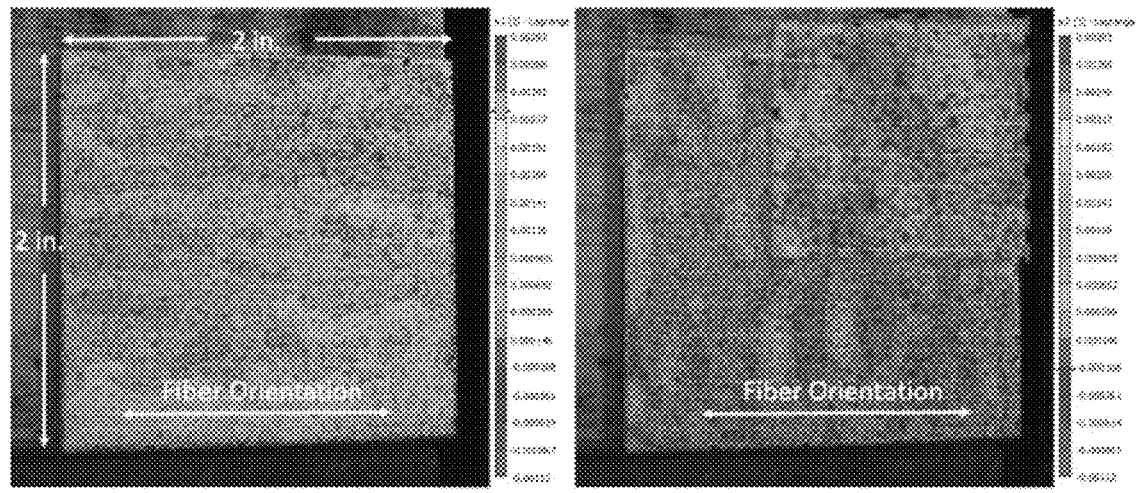
FIG. 5 is a set of graphical images showing the thermal expansion at 90° C. of a pultruded UD plate with the fiber orientation designated. The plotted vectors represent the orientation of the minor principle strain. Carbon fiber (CF) is unique with features such that the fibers either contract or remain same length with increase in temperature. Thus, for carbon fiber reinforced composites, tracking minor principal strain after evaluating thermal loading response provides a method to identify its orientation representing average through thickness effects for a planar material form.
Figure 6:
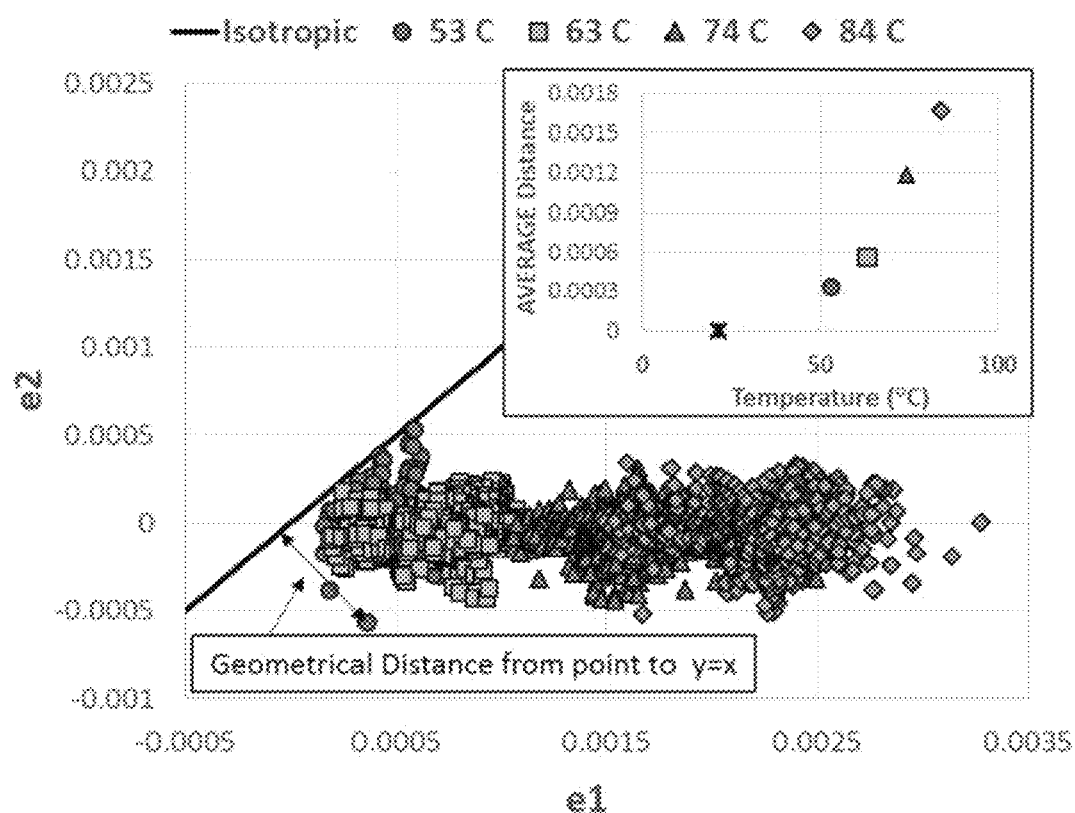
FIG. 6 is a plot showing principle strains developed in the UD plate with successive heating increments. As the plate strain states drift from isotropic with additional heat loading, the orientations derived from minor principle directions become more reliable.

Coupon scale parts were extracted from complete molded parts shown in FIGS. 4A and 4B, painted solid white with black speckle, and then isothermally heated to 90° C. for at least 30 min. Part dimensions are shown in FIGS. 4A and 4B. Images of the surface pattern were taken at room temperature before heating and then quickly (<10 s) after removing from the oven. 3D image correlation was then performed between the cool and thermally loaded surfaces to obtain a 2D surface thermal deformation map. FIG. 5 shows the 2D surface principle strain distributions with the vectors of the minor principle strain plotted on top. The orientation of the minor principle strain matches the fiber orientation due the description of the thermal expansion state described graphically in FIGS. 2, 3A, and 3B. It is postulated that for thin parts the dominate orientation, if any, can be extracted by the same method even for more complex parts The development of sufficient contrast that can be tracked by DIC upon thermal loading is demonstrated in FIG. 6, where the spatial principle strains at discrete 1 mm intervals were plotted against each other. This procedure was repeated with increasing temperatures from 53° C. to 84° C. and clearly demonstrates at 74° C. the captured surface has sufficient mobilization of thermal strains to be detected by DIC. The general trend is that all data points appear to move along the horizontal axis with increasing temperature, as the epoxy thermal expansion dominates the response. Because the CTE of carbon fiber is much smaller along its axis than that of epoxy, the direction of the fiber will always be the orientation of the minor principle strain (Pradere, C. and C. Saucier, *Transverse and Longitudinal Coefficient of Thermal Expansion of Carbon Fibers at High Temperatures* (300-2500 K). Vol 46. 2008. 1874-1884). The distribution of strains states likely indicates a variation of volume fractions spatially across the UD plate, but regardless of this unknown the principle axes developed during thermal loading remained unchanged, such that the magnitudes of thermal expansions are negligible given that sufficient expansion is observed. FIG. 6 graphically demonstrates the geometric distance of each point from the line y=x, which is a strong indication of development of anisotropic thermal expansions as a result of high orientation states. For more complex parts with many orientations present, this parameter is used to assess the reliability of the assumption that the alignment of the minor principle strain direction is the fiber axis. In particular, the further the distance the strain state is from isotropic, the more confidence one can have in the calculation of TDIC orientation.

Figure 7:
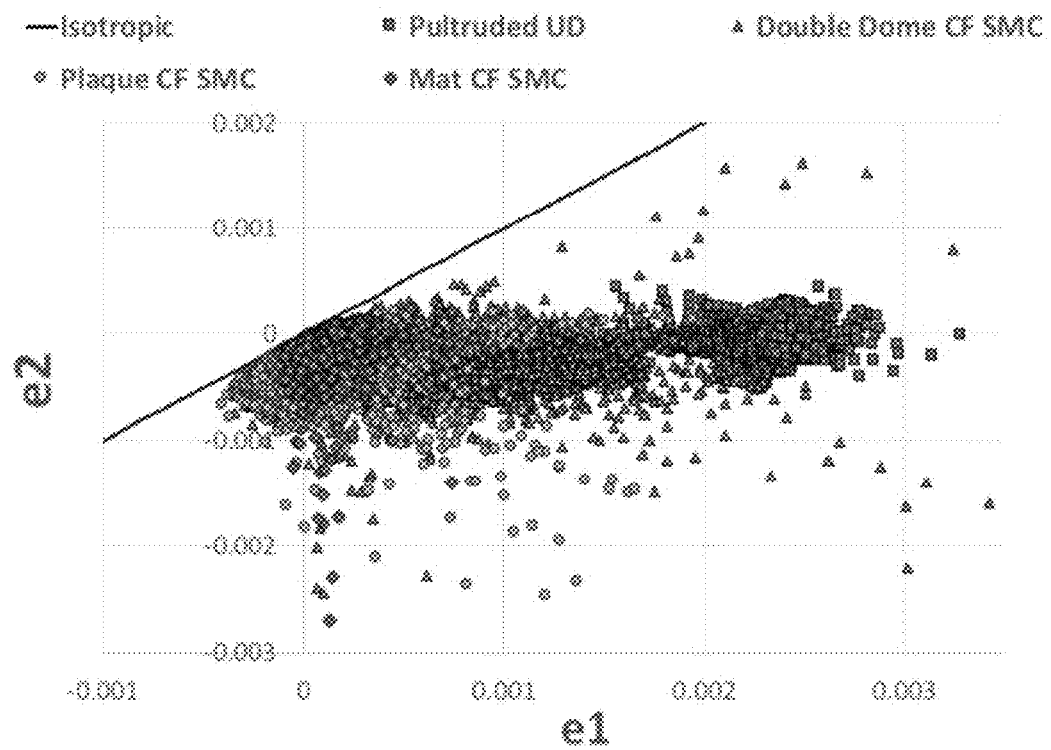
FIG. 7 is a plot of spatial principle strain states over the surface of 3 molded carbon fiber SMC samples and a pultruded UD carbon fiber sample. The larger the distance from the isotropic line a point is, the stronger orientation at that point.

In accordance with the presently disclosed subject matter, this Example establishes a measurement approach to detect regions of high orientation non-destructively for parts with complex manufacturing processes where orientation states are critical to performance but are likely unknown. FIG. 7 applies the similar analysis done in FIG. 6, but for samples with many more orientation states present. Conceptually, it is expected that sample surface strain states with little orientation developed during manufacturing processes would remain close to isotropic thermal expansion behavior. This was observed for the Mat CF SMC and for most strain states in the plaque CF SMC. However, in the double dome CF SMC more anisotropic thermal expansion behavior was observed. This would be expected due to the central placement of charge density for this part, which required more material flow to completely fill the mold. The flow of material produces regions of high orientation, which are being observed via TDIC as a result of their anisotropic thermal expansion behavior.

Figure 8:
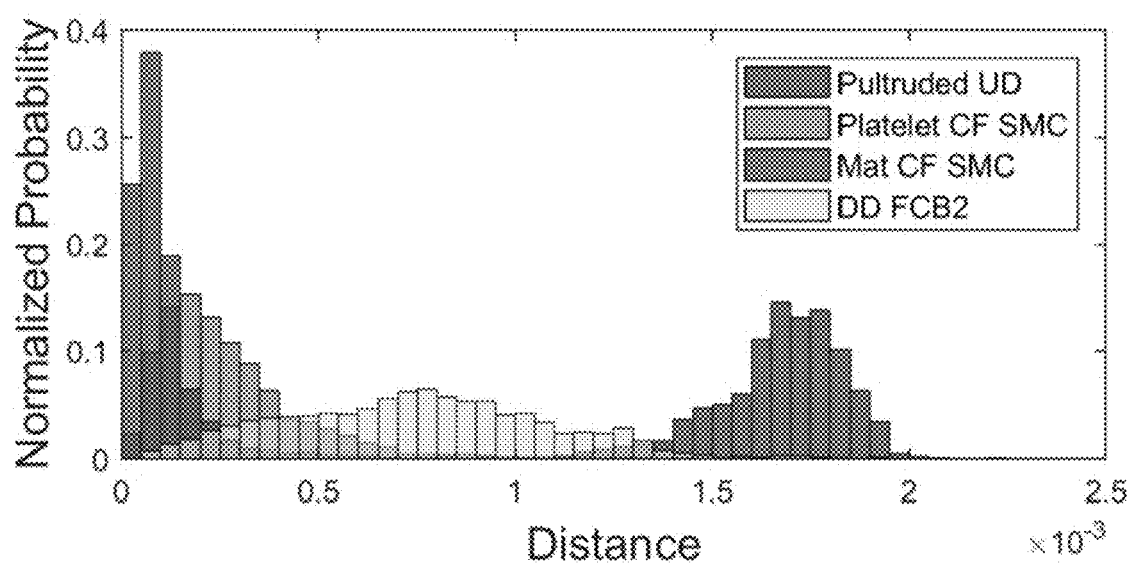
FIG. 8 is a bar graph showing the distribution of the geometric distances from isotropic of the spatial strains states present in FIG. 7. It is suspected that a distance>0.5e-3 will represent regions of high orientation for the materials discussed here and similar thresholds can be developed for various other reinforcing fibers and matrix resin system and can include ceramics and meatal matrix composites.

The magnitudes of the anisotropic thermal expansion states from FIG. 7 are captured in their distances from isotropic expansion shown in FIG. 8. This gives a clear picture of the total orientation present inside each part. The Mat CF SMC can be considered the nearly isotropic case, while the pultruded UD sample is completely oriented. In between these two lies the strain states for the flat plaque and the double dome. The flat plaque has some regions of orientation develop, but all regions remain below the orientation magnitudes of the pultruded UD sample. However, the double dome, which comprise the same material system as the flat plaque, clearly has regions of high orientation, even areas overlapping with the pultruded UD. Thus, the increased material flow necessary to form this part creates regions of high orientation, which can be readily captured by TDIC, giving design engineers a rapid feedback tool for molded part design and validation. Without being bound by a particular theory of operation, FIG. 8 suggests a cutoff threshold in distance magnitude at which the orientation derived from TDIC is the actual orientation observed in the part.

Conclusions

In accordance with the presently disclosed subject matter, this Example shows a novel technique, Thermal Digital Image Correlation (TDIC), for the rapid determination of internal orientation for fiber reinforced plastics. In exchange for the precision of optical microscopy or tomography techniques, the TDIC approach gives fiber orientation over a large area, like entire parts, making this an excellent tool for quality control and part development. A graphical parameter is introduced here that references the quality of determined orientations from the TDIC and is linked with the ability of this technique to accurately detect fiber orientation. This parameter graphically demonstrates the geometric distance of each point from the line that corresponds to equal thermally induced strain along major and minor principal strain directions, (for example, FIG. 6) which is a strong indication of development of anisotropic thermal expansions as a result of high orientation states. For more complex parts with many orientations present, this parameter is used to assess the reliability of the assumption that the alignment of the minor principle strain direction is the fiber axis. In particular, the further the distance the strain state is from isotropic, the more confidence one can have in the calculation of TDIC orientation.

Example 2

Routes to Mesostructure Characterization of Composites Using Discontinuous Prepreg and Mechanical Performance Chopped carbon fiber platelet-based epoxy infused prepreg material as Sheet Molding Compound is used in this Example for rapid compression molding of high-volume and complex automotive parts. These composites demonstrate impressive mechanical performance of near 40 GPa tensile modulus and 300 MPa strength based on coupon samples extracted from compression molded flat plaques. This Example evaluates the microstructure of this new material system both qualitatively and quantitatively in three dimensions. Physically important quantities for fiber reinforced composites corresponding to spatially varying platelet (chopped fiber bundles) orientation and fiber volume fraction are evaluated using advanced characterization methods including non-invasive X-ray microcomputed tomography, optical microscopy, and a novel method in accordance with the presently disclosed subject matter, Thermal Digital Image correlation (TDIC). Understanding the microstructure at multiple length scales and the process to property conditions through which certain performance criteria are met is an objective for this Example. Such detailed material science leads to tailored processing conditions for a targeted complex automotive component without the need for multiple characterization studies for molded parts of varying size and complexity.

To probe the microstructure and performance of this epoxy and carbon fiber-based platelet material system, 100 mm×12 mm coupons were extracted from 300 mm×300 mm flat plaques and front multiple flat locations of a molded double dome geometry (a component with very complex shape). Due to the flow of reinforced epoxy platelet-based charge material during compression molding, significant microstructural changes occur spatially for the double dome part that are not present in the flat plaque geometries. Regions of high platelet orientation normal to loading direction and regions with low fiber volume fraction resulting from material flow during compression molding provide lower bound properties in terms of tensile modulus and strength. The morphology of intact platelet structure that was observed for simply geometrical shape corresponding to a flat plaque (resulting in very strong tensile properties) did not translate for complex shaped compression molded parts such as a double dome. This insight provides for the optimization of mechanical properties of complex shaped components from chopped carbon fiber-based platelet charge and its optimization.

Carbon fiber composites offer tremendous application potential for transportation materials due to their excellent specific strength and modulus, improving energy efficiency. The most common limitation regarding the implementation of composite materials is cost, which includes both the acquisition of raw materials and the manufacturing these into usable parts. Recently, developments in manufacturing techniques have demonstrated significant improvements in the processability of carbon/epoxy based composite systems and increased the application space by developing a rapid manufacturing process for complex part geometries without the need for substantial retrofitting of current infrastructure. This manufacturing approach relies on the use of platelet-based carbon SMCs (sheet molding compounds) processed using compression molding techniques to near net shape with minimal post processing rapidly.

In some aspects, this Example demonstrates the validation and performance of parts with complex geometries and the methods of characterization. The chopped fiber platelet system has been geometrically and chemically optimized for performance and rapid production. The goal of this material system is to compete with other energy efficient and lightweight materials currently being utilized in automotive space, such as aluminum alloys. Target mechanical performance has been selected at 300 MPa failure strength and 40 GPa Young's Modulus in tension. Initial testing using materials extracted from 300×300 mm flat composite plaques have achieved these targets consistently. Currently, primary material parameters necessary for those benchmarks to be achieved in a molded complex part at sufficiently large scale and expected geometric complexities are being determined. In some aspects, this Example involves defining spatially the fiber orientation state and developed microstructure from a complex shaped part that mimics a production part at large length scales and desired manufacturing rapid cycle time.

Carbon fibers are mechanically anisotropic with significantly higher modulus along the fiber direction compared to transverse or radial direction. Failure initiation sites for fiber reinforced composites occur along the fiber matrix interfaces, making the failure strength significantly lower transverse to the fiber direction (Isaac M. Daniel, O. I, *Engineering Mechanics of Composite Materials*. 2nd ed. 2005: Oxford University Press.). Hence, the first area of interrogation for this platelet based composite system would be to determine if the part has preferred orientation or if the platelets are distributed randomly after manufacturing for a given geometry of the part and molding conditions associated charge placement, processing variables, and the amount of flow necessary for successful part filling. It is thought that the initial charge pattern is close to random, but due to pressure generated flow, it is probable that fibers will reorient along the flow direction. When the final material deviates from the orientation present originally with the initial charge, material performance is significantly altered. Three techniques are used herein to understand the material orientation state: X-Ray Computed Tomography (XCT) with image processing for non-invasively obtained three-dimensional orientation, traditional optical microscopy approach on extracted and polished samples with information limited to small regions of interest and in two-dimensions, and surface based Thermal Digital Image Correlation (TDIC), an approach provided in accordance with the presently disclosed subject matter. XCT creates a 3D density of map of the sample to distinguish between matrix and resin phases. However, the density between the two phases present in the composite, carbon fiber-based platelets and cured epoxy resin, is small, which limits the achievable contrast for direct segmentation-based measurements. After the data was acquired, the composite processing toolbox in commercially available VGstudio™© software was used to map out orientations spatially over a predefined mesh. TDIC is a technique where a sample is thermally loaded below its glass transition temperature, while the surface deformations are monitored. A custom prost-processing of these deformations can then be used to interpret local platelet dominant orientations if present. Lastly, optical high magnification digital microscopy is a destructive technique that uses polished specimens on certain planes under a microscope. Typically, orientations can then be determined by observing the elliptical geometry of round fibers.

However, the low-cost carbon fibers used in this Example are kidney bean shaped, as shown in FIG. 10A, and cannot be analyzed with existing published techniques that rely on relating orientation to the elliptical nature of the fiber (Lee, Y., et al., Materials Research Innovations, 2002. 6(2): p. 65-72). Thus, an approach in accordance with some aspects of the presently disclosed subject matter involves grey-scale intensity changes driven by the reflective nature of light from rotated planes in carbon fiber using a laser microscope. This technique assumes the fibers orientations are primarily in the plane of the thin part being observed. However, since an accurate cross-section of the fiber is no longer necessary, low mag images can be used increasing the field of view. This technique is readily automated to analyze dense fiber volume fraction with touching fibers and a suitable algorithm, described as follows, was developed for removing matrix/fiber boundaries. Polished samples of fiber reinforced composites are imaged under optical microscope or laser scanning microscope. The images are obtained at suitable magnification to clearly see the individual fibers whose equivalent diameter is represented digitally using, for example, a minimum of 6 to 20 pixels using uniform lighting conditions. The contrast of resin and fiber phases is identified by the corresponding differences in intensity values from reflection images. Multiple images are then stitched using automated x-y stage movement to collect resultant master image of target field-of-view that provides sufficient representative sample surface for analysis. Such images are then analyzed using image analysis software (examples are described herein below) and data synthesized for corresponding orientation information. See also FIG. 19.

Presented in this Example is the mechanical performance of tensile coupons extracted from molded flat plaques (FIG. 4A) and double domes (FIG. 4B). These two parts offers a stark difference in the internal development of microstructure as function of molding conditions utilized. The goal is to relate the spatial variation of mechanical properties to the changing internal microstructure induced from the material flow using the tools described herein. A relationship between the evolution of the microstructure under induced flow and the resulting mechanical properties allows engineers to tailor the charge and molding process to meet performance criteria in critical zones in a predictive fashion.

Results/Discussion
Mechanical Performance

Figure 11:
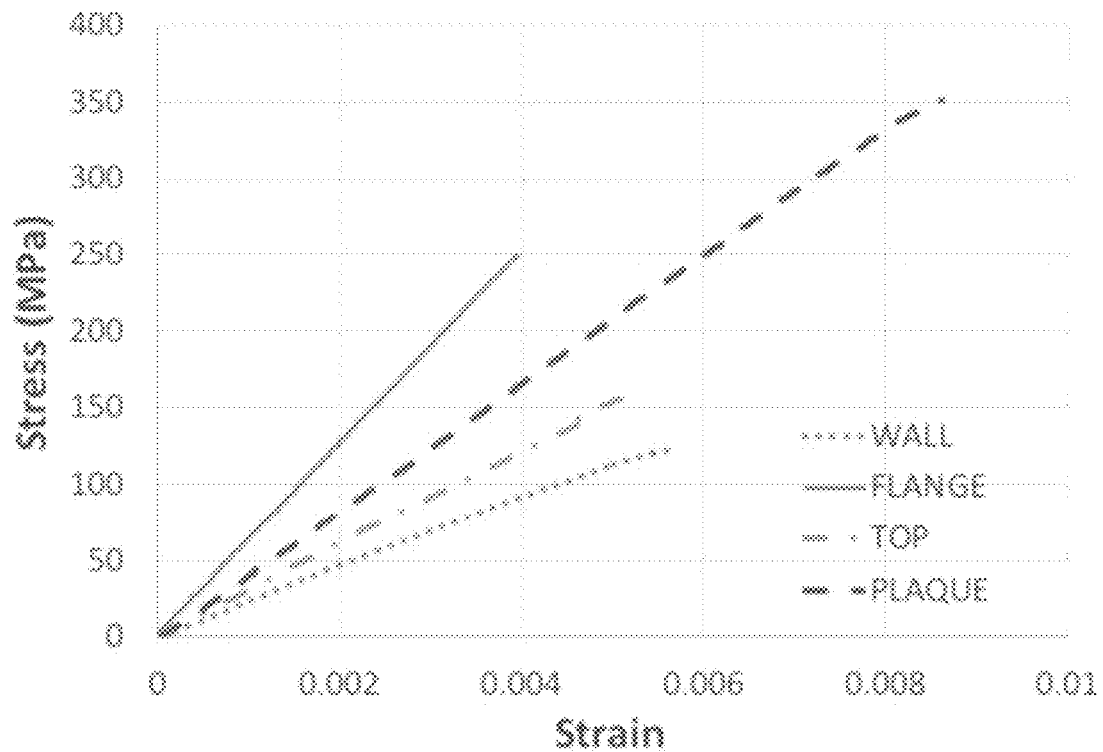
FIG. 11 is a line graph showing stress/strain response of tensile coupons extracted from molded flat plaques and the locations the double dome, demonstrating typical mechanical performance observed for these regions, differences mainly coming from varying local fiber orientations and matrix rich regions. The greater modulus for the flange and lesser modulus in the wall indicates a reduction in fibers orientation along the tensile axis of the coupon.
Figure 12:
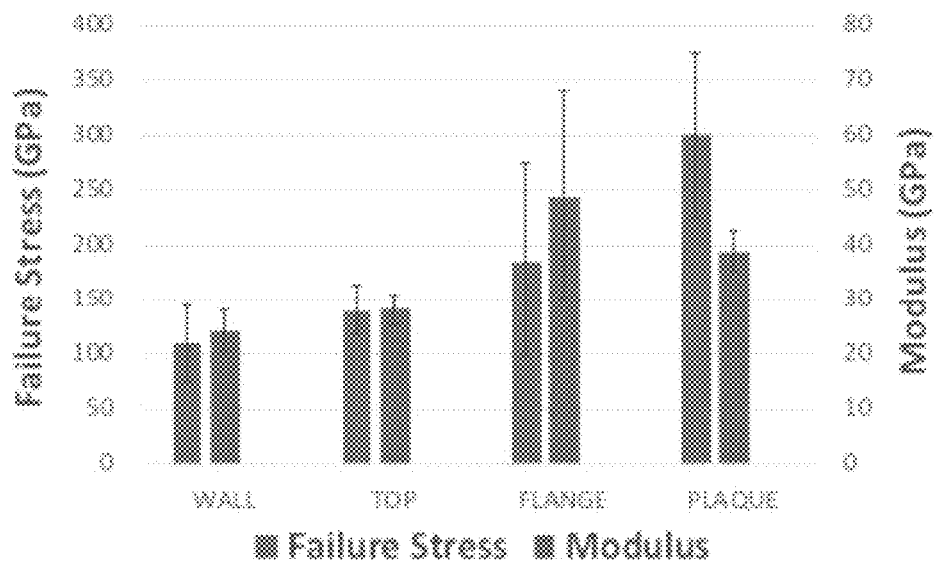
FIG. 12 is a bar graph showing average behavior of tensile coupons tested. The highest failure stresses come from the coupons extracted from the plaque parts, which require less material flow to complete the part and thus had less variations in matrix rich regions and had similar fiber orientations spatially.

Tensile coupons (100×12 mm) were extracted from the flat plaques at three locations from the double dome which allowed for 50.8 mm gauge region and 25.4 mm grip region. The double dome regions included in this Example correspond to locations identified as top, wall, and flange, as shown in FIG. 4B. The 100×1.2 mm coupon is smaller than the suggested in ASTM 03039 standard, but in order to study the internal structure at 15-micron voxel resolution for XCT studies prior to mechanical loading non-invasively, a smaller sample was necessary (ASTM, *ASTM 03039 I 03039M-17 Standard Test Method for Tensile Properties of Polymer Matrix Composite Materials.* 2017). Two tomography scans were utilized to cover the complete 50 mm gauge length at the target resolution which was chosen for several reasons. The flat plaque tensile tests demonstrated properties on par with the target mechanical performance. The average failure stress and modulus were found to be 300 MPa and 39.0 GPa. However, the mechanical performance for the same material molded in the double dome part with severe geometric complexities demonstrated a large variation in measured modulus and failure strength in tension. A graphical presentation of the general stress/strain behavior is given in FIGS. 11 and 12. This shows that the highest modulus behavior was obtained in the flange and lowest modulus in the wall for those samples extracted from the complex part. All double dome samples, regardless of extraction location, were found to have lower failure stress than the flat plaque.

Figure 13:
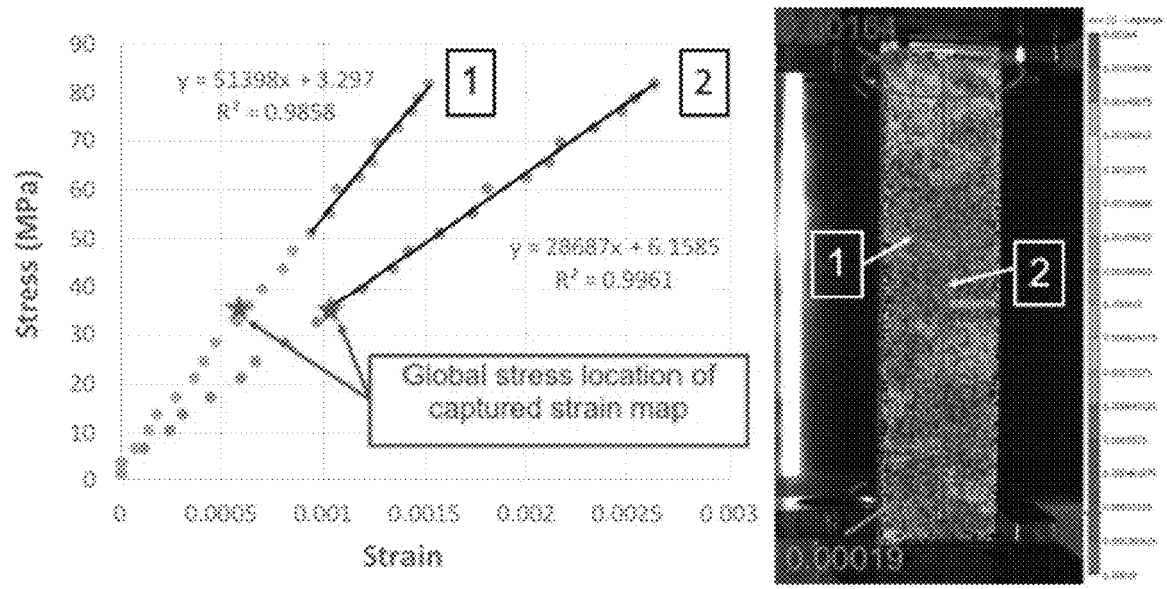
FIG. 13 is a graph (left panel) and a graphical image (right panel) showing stress/strain behavior of a tensile coupon from the flange section (sample FBD1) of the double dome with the strain map at the staffed stress position. A significant strain concentration where the sample ultimately failed is observed at the top.
Figure 14:
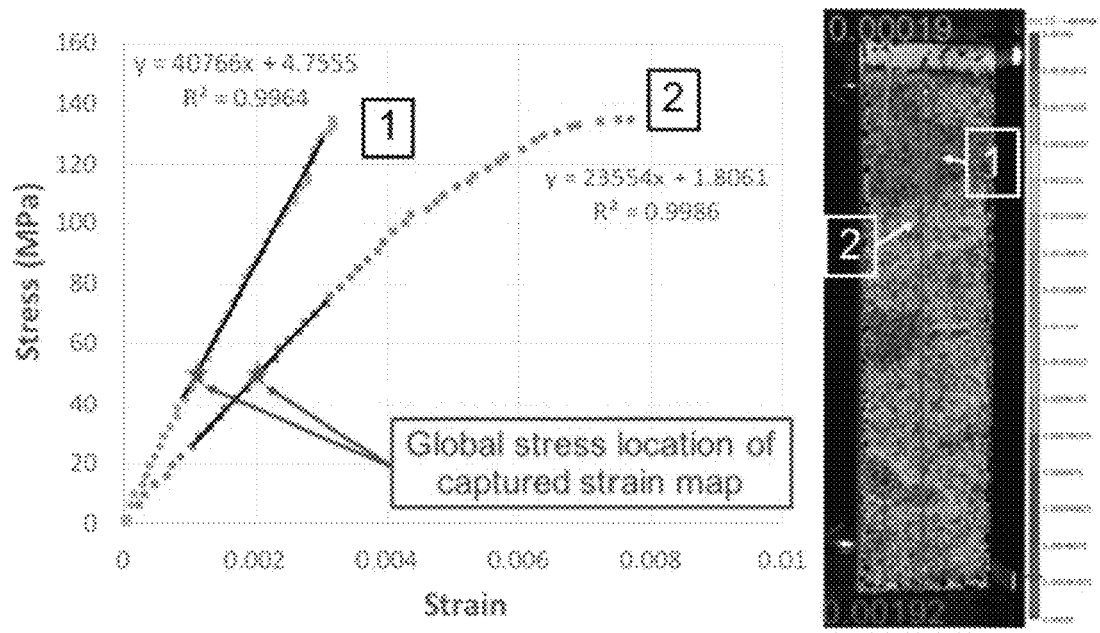
FIG. 14 is a graph (left panel) and a graphical image (right panel) showing stress/strain behavior of a tensile coupon from the wall section of example double dome component (sample WBD2) with the strain map at the starred stress position. This sample broke in the mid-point where a congregated region of transversely oriented fibers was located and confirmed using TDIC method for its fiber orientation detection.

Strain on the tensile coupons was measured using Digital Image Correlation (DIC) through a commercially available software, Vic3D by Correlated Solutions. The surface strain maps obtained demonstrated significant spatial variability as a result of high orientation regions and the density of platelets. Hence, the gage region over which the modulus is measured can have a significant impact on the reported result. For this reason, two points located on both ends of the gage region were selected to be reference points for the optical extensometer, which measures the relative displacement of these points and calculates the engineering strain encompassing the entire sample. A demonstration of high strain region and low strain region and the resulting modulus is given in FIG. 13 and FIG. 14. These figures show spatial variation of tensile strain in the axial direction along the length of the sample using lower resolution 30-DIC acquisition conditions. As will be seen later, DIC images are acquired at high resolution for obtaining spatially resolved transverse strains.

Fiber Orientation by Tomography

Figure 15:
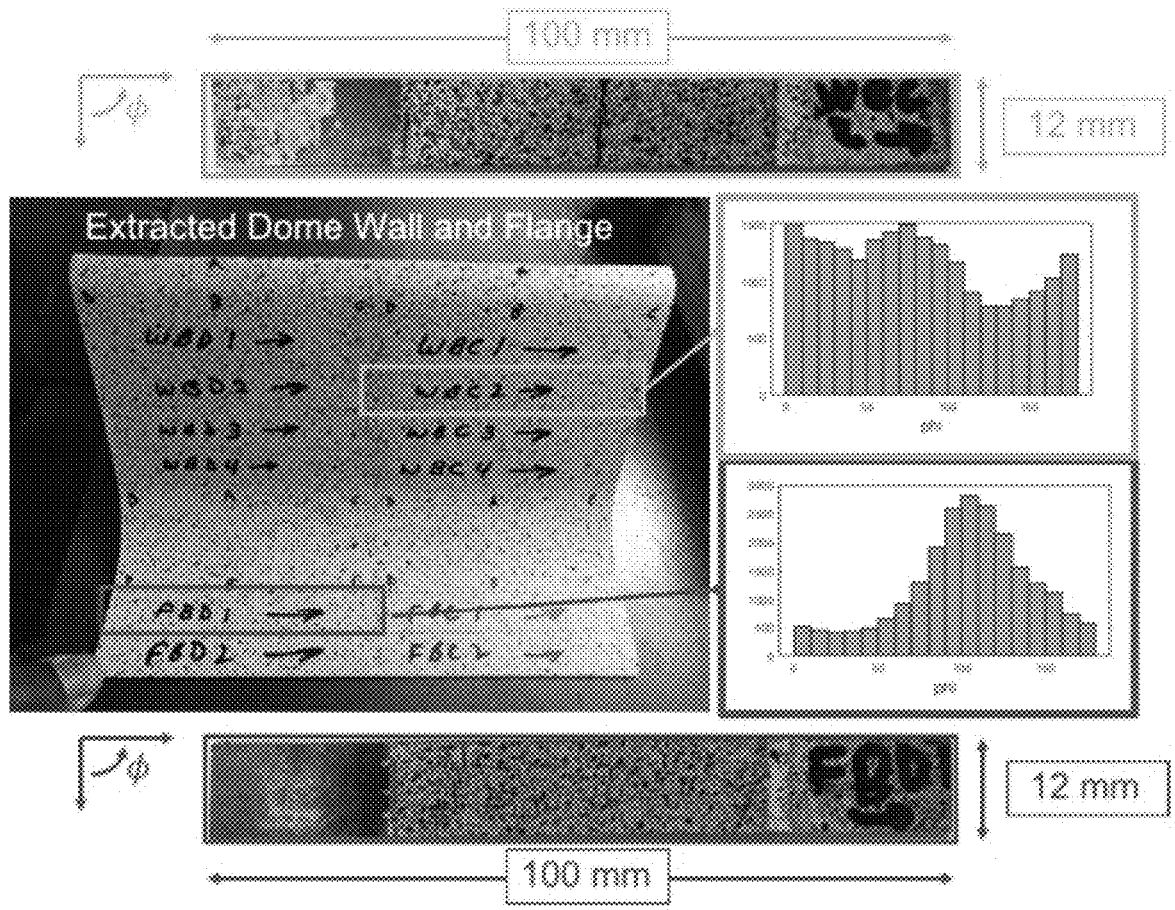
FIG. 15 is a set of images and histograms of all mesh elements from the analyzed tomography data for two locations on the double dome, demonstrating the direction of material flow during compression molding. X-ray computed tomography was used to have an additional independent measurement scheme to confirm fiber orientation and matrix rich region identification from TDIC method.
Figure 16:
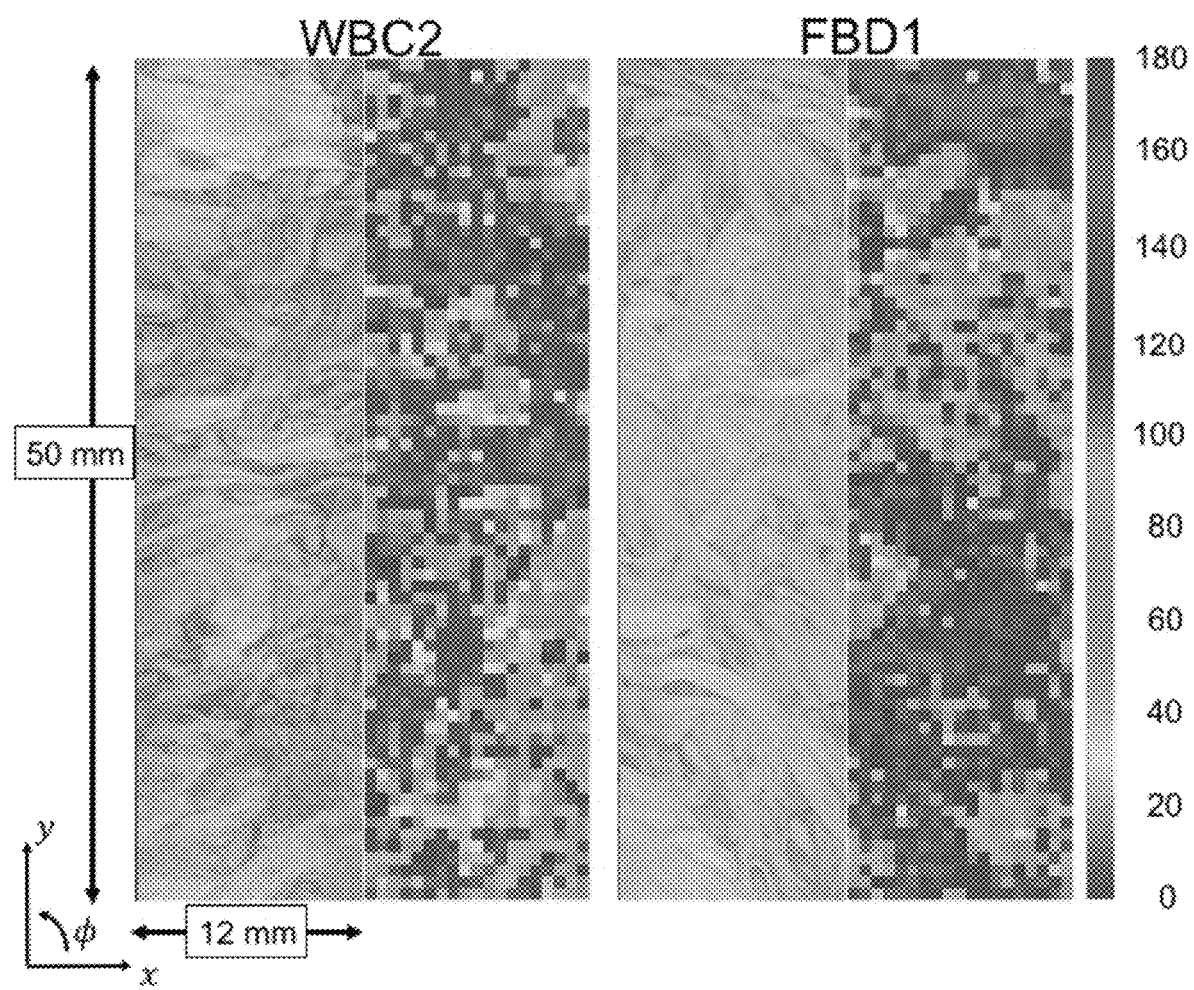
FIG. 16 is a graphical image showing an example of tomography and corresponding orientation map obtained after analysis for two parts on the double dome. The large areas of mis-orientation (i.e. warm colors) with the tensile axis of the coupon correlate well with high stain and failure zones.

To determine the internal orientation of these platelet based SCM carbon composites, two XCT scans were captured over ~25 mm sample windows at 15-micron voxel resolution and stitched together. The typical fiber size is on the order of ~8 microns and thus, a single voxel is slightly larger than 'average' diameter of carbon fiber. Hence, the tomographic reconstructions are dependent on depicting the spatial arrangements of the macroscopic platelet structure. Thus, the intent is not to map single fiber orientations (Benjamin R. Denos, S. G. K., R. Byron Pipes, *Progressive Failure Analysis in Platelet Based Composites Using CT-Measured Local Microstructure*, in SAMPE. 2017). This approach provides desired information of microstructure at suitable length scales and represents statically significant region of volume for the related analysis. The acquired tomographic data is then processed in the Fiber Composite Analysis Module in VGStudio™©. An average orientation tensor is calculated for each mesh element in a 3D mesh overlay on the specified sample region. Mesh elements in this study were 0.7×0.7×0.1 mm, which produced approximately 20 spatial orientation maps through the ~2.0 mm thickness. The fiber direction corresponds to the Eigen vector associated with the maximum Eigen value of the orientation tensor. Extracting the coupon specimens defined in FIG. 15 and calculating the orientations as described, the global histogram of all mesh element fiber orientations is plotted. The shape of these histograms gives insight into the flow behavior of the carbon fiber SMC during compression molding. As the charge pattern was centrally weighted in the mold, platelets flowed from the center of the double dome to the ends, which is captured in the histograms. Additionally, due to the boundary condition along the mold edge, the flange coupon revealed greater orientation along its axis, as material flowed parallel to edge of the mold. FIG. 16 demonstrates a tomography slice with the corresponding orientation map for the two regions on double dome shown in FIG. 15. Observing the high strain and failure locations on the coupons from DIC strain maps during tensile testing in FIG. 13 and FIG. 14. It is clear these regions correlate well with the locations of orientation transverse to the tensile axis.

Thus, transverse loading to regions of high orientation produce high strains and failure locations. These regions develop when the material flows inside the mold during compression molding and indicate the likely cause for the decreased failure stress in the double dome compared to the flat plaque parts for the considered loading direction or strain path.

Thermal Digital Image Correlation

Figure 17:
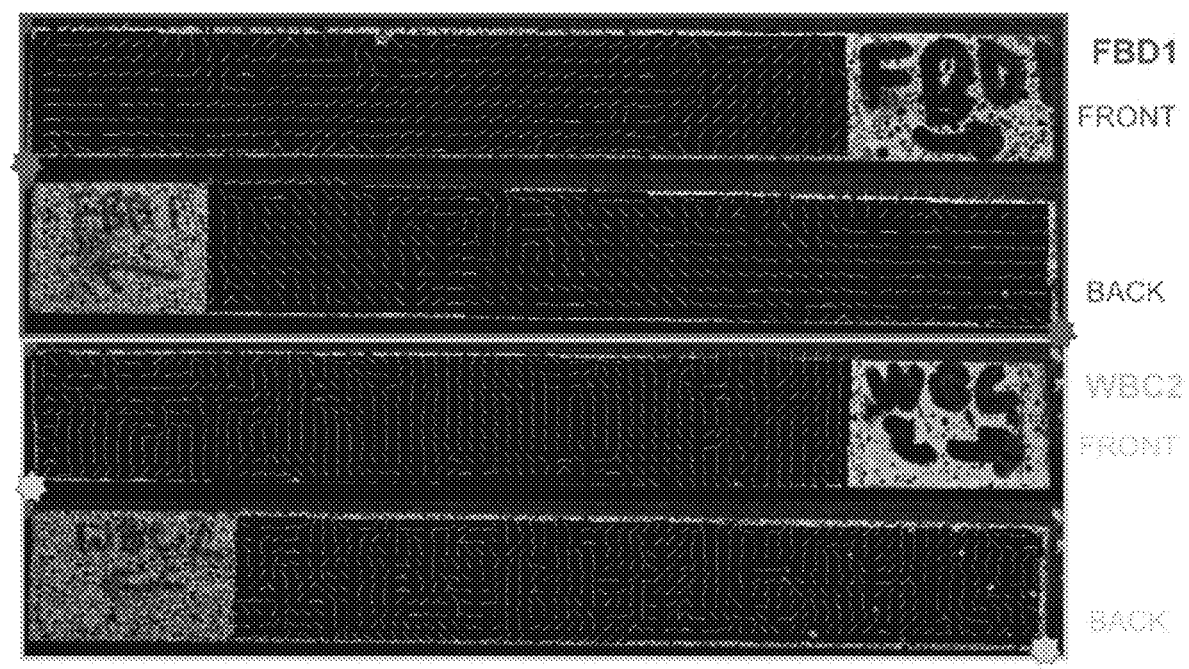
FIG. 17 is a set of images showing surface vector maps of fiber orientations obtained from the TDIC technique. The stars represent the same corners when the samples are imaged on the front and the back. This technique gives useful insight into the global orientation flow patterns in particular region of a large part.
Figure 18:
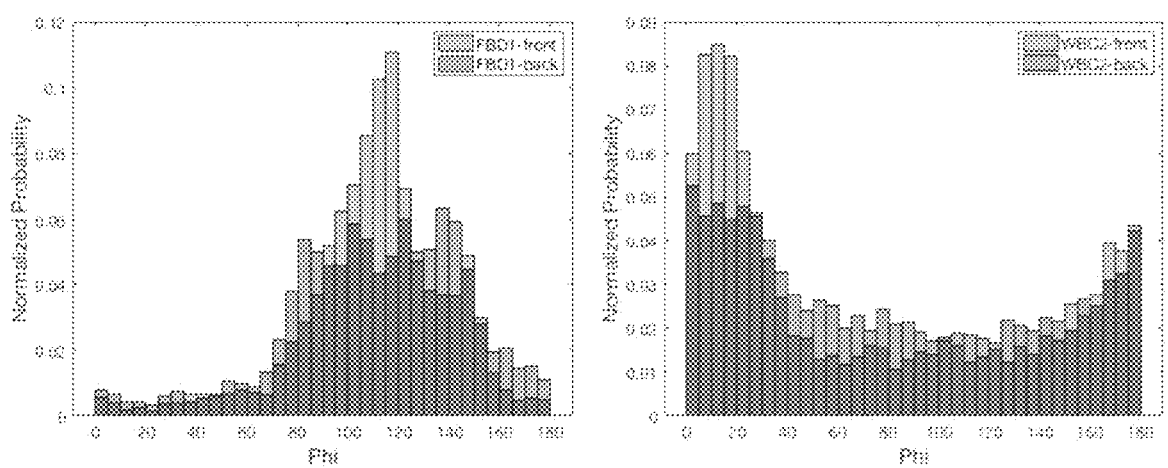
FIG. 18 is set of bar graphs showing the distribution of orientation angles for Wall (WBC2) and Flange (FBD1) samples from TDIC for both front and back of the coupon. The corresponding green and red stars represent the same corners after the sample has been flipped over. These plots suggest the general orientations from TDIC match well from front to back and with the histograms for these samples from high resolution x-ray computed tomography in FIG. 15.

In accordance with the presently disclosed subject matter, Thermal Digital Image Correlation are used specifically for this material system in order to rapidly evaluate the preferred orientations spatially and validate large parts non-destructively. In some aspects, the approach seeks to detect isotropic mechanical thermal expansions, which arise from highly orientated fiber regions. Carbon fibers, which have a negative thermal expansion along their axis and have highly anisotropic response to thermal loading, and epoxy, which has a relatively large isotropic thermal expansion, are ideal candidates for sensitivity to this testing technique due to the contrast in their Coefficient of Thermal Expansion (CTE). For the tests performed here, parts were speckled with spray paint to obtain a trackable surface pattern, heated to in an oven for 30 min at 90° C. (or until they were isothermally loaded), and then imaged for DIC. For industrial practice, the technique can easily be integrated into production by monitoring the cooling rather than subsequent thermal loading. Initial results suggest that excellent orientation mapping can be achieved with this surface only, approximate method, and in the least, regions of strong orientation can be identified over large areas. The fiber orientation vectors obtained from the presently disclosed TDIC technique are shown in FIG. 17 for both the front and hack surfaces of the same parts for which tomography data was presented in FIG. 16 for select regions based on extracted samples from those locations using high resolution X CT. A histogram of all the surface orientations obtained across the front and back of the coupons by TDIC is shown in FIG. 18. Notably, the distributions from font and back match well and appear to correspond well with platelet orientation histograms obtained from a very precise X-ray tomography technique identified in FIG. 15. These orientation vectors and histograms replicate the known manufacturing conditions, specifically that the charge material was densely placed in the center of the double dome part and flowed off the top of the double dome toward center flange and the end flanges.

Optical Microscopy and Digital Image Analysis

Directly observing the surface by optical microscopy provides the most reliable method to date to confirm the orientation and internal microstructure, which includes the deformation associated with pre-molded platelets and any development of resin rich pockets which is undesirable. However, for orientation evaluation in three dimensions of non-circular fibers, like the low-cost carbon fibers used in making the platelets for this Example, considering only the two-dimensional optical images, currently there is no established method. Thus, demonstrated here in this Example in accordance with some aspects of the presently disclosed subject matter is a quick and simple approach to determine the fiber orientation for non-circular cross-sections using the variation of grey-scale intensity in relation to the orientation of considered plane of optical images. The goal is to capture the high intensity reflection using a monochromatic laser of the more orientated fibers against the low intensity reflection of fibers perpendicular to the polished surface and scale that intensity change as predominately associated with in-plane fiber orientation changes, the angle phi as described in FIG. 16. Hence, out of plan orientation is neglected, which is appropriate for composite parts with small thickness typically below 5 mm. A significant advantage is that stitched images using lower magnifications can be utilized (for example ×20), increasing the field of view, since only a few pixels are necessary to obtain a cross-sectional intensity rather than many pixels necessary to accurately measure the cross-sectional area.

Figure 19:
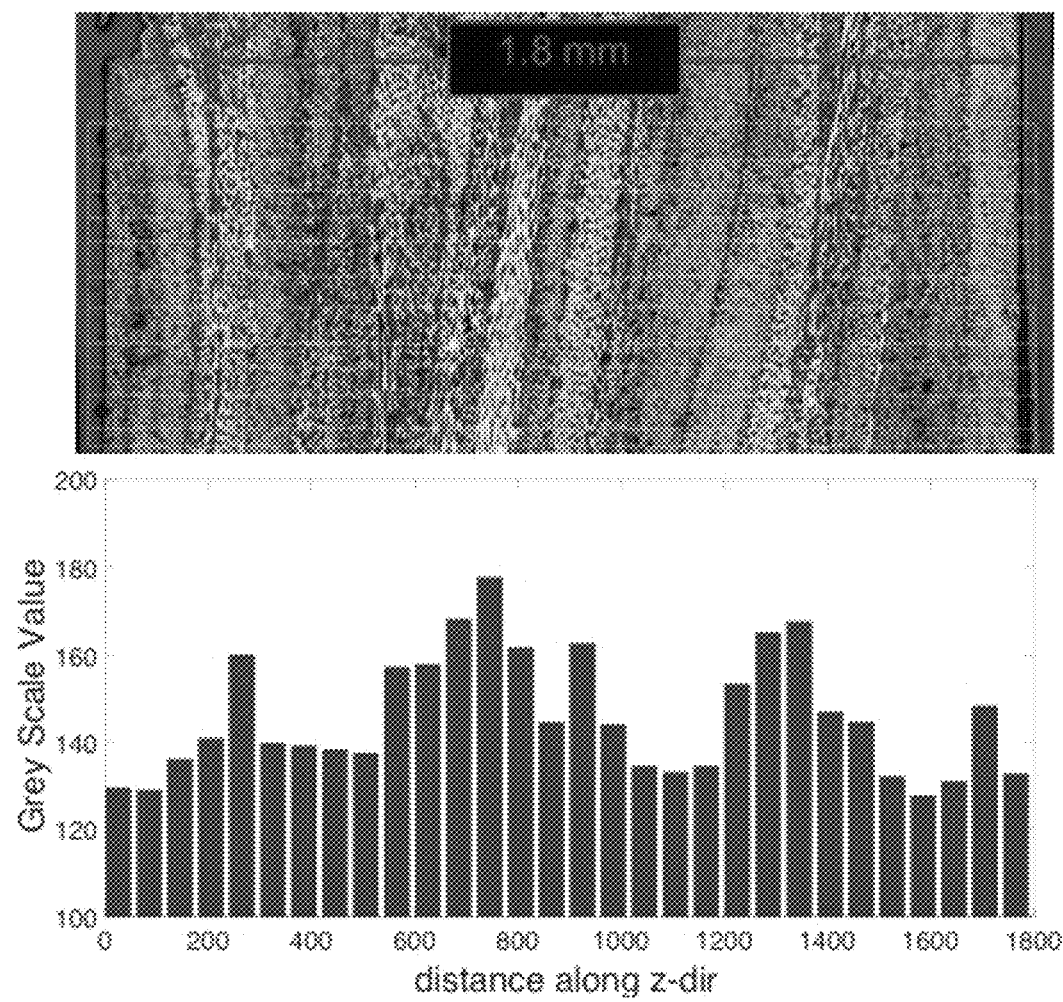
FIG. 19 is an image and a bar graph showing that stitched images using lower magnifications can be utilized (for example ×20), increasing the field of view, since only a few pixels are necessary to obtain a cross-sectional intensity rather than many pixels necessary to accurately measure the cross-sectional area.

FIG. 19 documents example results from this approach. An automated method was quickly established for routine implementation of this approach that bins fiber intensities over a specified width, eliminating pixels with intensities that are below a threshold value which represents the matrix phase. When this method is applied to the fiber cross-section in FIG. 19, excellent correlation is obtained locating fibers of high mis-alignment with the polished surface.

This approach can be rapidly adapted to compare with orientation data obtained from large area with considered volume corresponding to tomography measurements, confirming and providing confidence in methods that are not directly based upon observing individual fibers.

Conclusions

The carbon fiber platelet-based SMC system, which favorably competes with aluminum as an alternative light weight engineering material, demonstrates strong potential for compression molded based automotive part manufacturing and continued refinement, and is capable of achieving superb mechanical performance, 300 MPa failure stress and 40 GPa modulus for flat plaques. Furthermore, complex geometry parts can be fabricated rapidly, at very competitive cycle times, using largely existing infrastructure of automotive manufacturing employing compression molding approach. The presently disclosed characterization methods are used in this Example to understand the performance of these materials in order to harness its complete potential in a predictive fashion. Platelet orientation has been identified as a parameter that plays a role in predicting the performance of these SMC material systems. Highly oriented regions of platelets develop where the material must flow to completely fill a mold without spreading. These can create weakness in mechanical properties transverse direction unless layers above and below this location can compensate similar to isotropic laminate design concept, and the detection of these locations often requires the destruction of the part using currently existing microscopy-based methods with very small field of view and extremely laborious effort. Thus, the mechanical characterization of large parts for quality control and performance benchmarks plays a role in rapid commercialization of the considered material system.

In addition, implementation of TRIC for manufacturing process control shows high promise for immediate commercial applications including the manufacturing/synthesis of reinforced thermoplastic and thermoset lamina, laminates, its variant form called organosheets, multi-step processing of metallic materials such microtextured Ti based alloys, metal-matrix composite sheet stock. By way of an additional, non-limiting example when aerospace grade prepreg or automotive organosheets are made, typically one starts from continuous fiber in a sheet or mat form and reinforces with resin in a continuous or batch process. Challenges still exist with respect to properly reinforcing resin, such as high temperature thermoplastics and high glass transition thermosets into small void or inter fiber and inter bundle spacing, while attempting to eliminate air or defects. A TDIC approach in accordance with the presently disclosed subject matter can be used as a part of manufacturing process control Additionally, methods of the presently disclosed subject matter, which employ Thermal Digital Image Correlation (TDIC), provided a solution to understand the orientation behavior of the carbon/epoxy-based platelets in a molded part. The presently disclosed methods are extremely fast, easily scalable for large part size, and can simply be implemented in a manufacture assembly line without the disruption of the manufacturing process, such as but not limited to a real-time manufacturing environment of fiber reinforced SMC type materials for structural applications in automotive space.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for assessing a characteristic of a composite material or a joint between two materials, the method comprising:
    applying indicia to a surface of the composite material or the joint;
    exposing the composite material or the joint to a temperature change;
    imaging the composite material or the joint at a plurality of time points before, during and/or after the temperature change using one or more optical cameras to measure strain and a thermal camera to measure spatially resolved temperatures of the composite material or the joint comprising the indicia, thereby monitoring a surface mechanical strain tensor while the composite material is undergoing the temperature change; and
    assessing the characteristic of the composite material or the joint based on the imaging.

2. The method of claim 1, wherein the composite material comprises a fiber-reinforced composite material.

3. The method of claim 2, wherein the composite material comprises a fiber-reinforced polymeric, metallic, or ceramic composite.

4. The method of claim 1, wherein the composite material comprises a laminate/fabric based multi-layer composite material or a molded discontinuous fibers/bundles/platelets based composite material.

5. The method of claim 1, wherein the composite material comprises a material selected from the group consisting of a thermoset-based carbon fiber, a thermoplastic-based carbon fiber, a glass fiber, a basalt fiber, a natural fiber, and combinations thereof.

6. The method of claim 5, wherein the thermoset-based carbon fiber comprises a material selected from the group consisting of an epoxy, a vinyl ester, a polyester, a phenolic resin-based polymer, and combinations thereof.

7. The method of claim 5, wherein the thermoplastic-based carbon fiber comprises a material selected from the group consisting of polyphenylene sulfide (PPS), polyether ether ketone (PEEK), acrylonitrile butadiene styrene (ABS), polyethylene terephthalate (PET), polypropylene, polycarbonate, polybutylene terephthalate (PBT), polyethylene, polyvinyl chloride (PVC), nylon, and combinations thereof.

8. The method of claim 1, wherein the joint is selected from the group consisting of a hybrid joint and an adhesively bonded joint.

9. The method of claim 1, wherein exposing the composite material to a temperature change comprises heating and/or cooling the composite material.

10. The method of claim 9, wherein cooling the composite material comprises allowing the composite material to cool after manufacturing.

11. The method of claim 1, wherein the imaging comprises identifying spatially varying temperatures, identifying measured surface strains, or a combination thereof.

12. The method of claim 1, wherein the indicia comprise a contrasting black and white (B/W) pattern.

13. The method of claim 1, wherein the imaging comprises using two optical cameras to measure strain.

14. The method of claim 1, wherein the assessing the characteristic of the composite material based on the imaging comprises assessing fiber orientation of continuous fibers through a volume of the composite material.

15. The method of claim 1, wherein assessing the characteristic of the composite material based on the imaging comprises identifying spatially varied fiber orientations, matrix rich regions, corresponding mechanical properties, or combinations thereof.

16. The method of claim 1, wherein assessing the characteristic of the composite material comprises assessing manufacturing process control, quality assurance and/or control; predicting thermal behavior and/or mechanical behavior; and/or evaluating a repair.

17. The method of claim 1, wherein the imaging further comprises obtaining multiple magnified optical images of a cross-section of the composite material or joint; and the method further comprises determining fiber orientation for a cross-section of the composite material or the joint using a variation of grey-scale intensity in the cross section of the composite material or the joint.

18. The method of claim 15, wherein the cross-section is a non-circular cross-section.

19. A method for assessing fiber orientation in a composite material or a joint between two materials, the method comprising:
    exposing a cross-section of the composite material or the joint to a light source;
    obtaining multiple magnified optical images of the cross-section of the composite material or the joint;
    detecting differences in grey-scale intensity values from the multiple images; and
    assessing the fiber orientation for the cross-section of the composite material or the joint based on the differences in grey-scale intensity values in the cross-section of the composite material or the joint.

20. The method of claim 19, wherein the cross-section of the composite material or the joint comprises a reinforcing element or material having a non-circular cross-section.

21. A method of manufacturing a composite material, the method comprising:
    during manufacturing of the composite material, applying indicia to a surface of the composite material and exposing the composite material to a temperature change;
    imaging the composite material comprising the indicia using one or more optical cameras to measure strain and a thermal camera to measure spatially resolved temperature at a plurality of time points before, during and/or after the temperature change, thereby monitoring a surface mechanical strain tensor while the composite material is undergoing the temperature change; and assessing a characteristic of the composite material based on the imaging.

22. The method of claim 21, comprising controlling the manufacturing of the composite material based on the assessing of the characteristic of the composite material.

* * * * *